(12) United States Patent
Costanzo et al.

(10) Patent No.: US 7,718,673 B2
(45) Date of Patent: May 18, 2010

(54) ISONIPECOTAMIDES FOR THE TREATMENT OF INTEGRIN-MEDIATED DISORDERS

(75) Inventors: Michael J. Costanzo, Ivyland, PA (US); William J. Hoekstra, Chapel Hill, NC (US); Bruce E. Maryanoff, Forest Grove, PA (US)

(73) Assignee: Ortho-McNeil Pharmaceutical, Inc., Raritan, NJ (US)

( * ) Notice: Subject to any disclaimer, the term of this patent is extended or adjusted under 35 U.S.C. 154(b) by 20 days.

(21) Appl. No.: 10/345,808

(22) Filed: Jan. 16, 2003

(65) Prior Publication Data

US 2003/0181440 A1 Sep. 25, 2003

Related U.S. Application Data

(63) Continuation of application No. 09/667,134, filed on Sep. 21, 2000, now abandoned.

(60) Provisional application No. 60/156,617, filed on Sep. 29, 1999.

(51) Int. Cl.
*A61P 9/00* (2006.01)
*A61P 19/10* (2006.01)
*A61K 31/445* (2006.01)
*C07D 211/00* (2006.01)
*C07D 401/00* (2006.01)
*C07D 405/00* (2006.01)
*C07D 409/00* (2006.01)

(52) U.S. Cl. ............ 514/315; 514/318; 514/326; 514/330; 546/193; 546/208; 546/212; 546/214; 546/226; 546/245

(58) Field of Classification Search .......... 514/315, 514/318, 326, 330; 546/193, 208, 212, 214, 546/226, 245
See application file for complete search history.

(56) References Cited

U.S. PATENT DOCUMENTS

| | | | |
|---|---|---|---|
| 4,288,362 A | 9/1981 | Rolf et al. | |
| 5,352,667 A | 10/1994 | Lider et al. | |
| 5,576,334 A | 11/1996 | Brown et al. | |
| 5,602,155 A | 2/1997 | Ruminski | |
| 5,648,368 A | 7/1997 | Egbertson et al. | |
| 5,700,801 A * | 12/1997 | Pieper et al. | 514/253.01 |
| 5,703,050 A | 12/1997 | Klingler et al. | |
| 5,798,370 A | 8/1998 | Ruminski | |
| 5,817,677 A | 10/1998 | Linz et al. | |
| 5,922,717 A | 7/1999 | Pieper et al. | |
| 5,952,381 A | 9/1999 | Chen et al. | |
| 6,066,651 A | 5/2000 | Hoekstra | |
| 6,069,254 A | 5/2000 | Contanzo et al. | |
| 6,100,423 A | 8/2000 | Collins et al. | |
| 6,251,944 B1 | 6/2001 | Chen et al. | |
| 6,268,380 B1 | 7/2001 | Tjoeng et al. | |

FOREIGN PATENT DOCUMENTS

| | | |
|---|---|---|
| EP | 0373891 A2 | 6/1990 |
| JP | 4334357 A | 11/1992 |
| WO | WO 94/12181 | 6/1994 |
| WO | WO 95/08536 A1 | 3/1995 |
| WO | WO 95/32710 A1 | 12/1995 |
| WO | WO 97/06791 A1 | 2/1997 |
| WO | WO 97/08145 A1 | 3/1997 |
| WO | WO 97/23451 A1 | 7/1997 |
| WO | WO 97/36859 | 10/1997 |
| WO | WO 97/41102 A1 | 11/1997 |
| WO | WO 98/16512 A1 | 4/1998 |
| WO | WO 98/25892 A1 | 6/1998 |
| WO | WO 98/39325 A1 | 9/1998 |
| WO | WO 99/16758 A1 | 4/1999 |
| WO | WO 99/25685 A1 | 5/1999 |
| WO | WO 99/50249 A2 | 10/1999 |
| WO | WO 99/58501 A1 | 11/1999 |
| WO | WO 99/67230 A1 | 12/1999 |
| WO | WO 00/11022 A1 | 3/2000 |
| WO | WO 00/34255 A1 | 6/2000 |
| WO | WO 01/10867 A1 | 2/2001 |
| WO | WO 01/11002 A1 | 2/2001 |

OTHER PUBLICATIONS

Coleman, P.J. et al, Expert. Opin. Ther. Patents, 12(7), 2002, pp. 1009-1021.*
Fields, Gregg B. Expert. Opin. Ther. Patents, 8(6), 1998, pp. 633-644.*
Mousa, S.A.. Expert. Opin. Ther. Patents, 9(9), 1999, pp. 1237-1248.*
Posey, J.A. et al, Cancer Biotherapy, 19(2), 2001, 125-132.*
Cox, D. Curr. Pharm. Des., 10(14), 2004, pp. 1587-1596, MEDLINE abstract 15134557.*
Ibbotson T, McGavin JK, Goa KL, Drugs 2003; 63: 1121-63, MEDLINE abstract 12749745.*
Varon, David; Lider, Ofer; Dardik, Rima; Shenkman, Boris; Alon, Ronen; Hershkoviz, Rami; Kapustina, Galina; Savion, Naftali; Martinowitz, Uri; Greenspoon, Noam, Thrombosis and Haemostasis, 70(6), 1030-6 (English) 1993.*

(Continued)

*Primary Examiner*—Brenda L Coleman
(74) *Attorney, Agent, or Firm*—Yuriy P. Stercho

(57) ABSTRACT

The invention is directed to novel isonipecotamide derivatives of Formula (I):

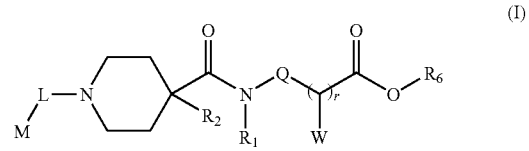

which are useful in treating integrin-mediated disorders.

17 Claims, No Drawings

OTHER PUBLICATIONS

S.A. Mousa et al., Emerging Theraupeutic Targets, 2000, 4(2), "Integrins as novel drug discovery targets: potential therapeutic and diagnostic implications", pp. 143-153.

W.H. Miller et al., Drug Discovery Today, 2000, 5(9), "Identification and in vivo efficacy of small-molecule antagonists of integrin $\alpha_v\beta_3$ (the vitronectin receptor)", pp. 397-408.

S.A. Mousa et al., Exp. Opin. Ther. Patents, 1999, 9 (9), "Antiintegrins as a potential therapeutic target in angiogenesis", pp. 1237-1248.

W.J. Hoekstra ,Current Medicinal Chemistry, 1998, 5, "Combinatorial Chemistry Techniques Applied to Nonpeptide Integrin Antagonists", pp. 195-204.

J. Samanen et al., Current Pharmaceutical Design, 1997, 3, "Vascular Indications for $\alpha v$ Antagonists", pp. 545-584.

D. Varon et al., Thromb. Haemostasis, 1993, 70(6), "Inhibition of Integrin-Mediated Platelet Aggregation, Fibrinogen-Binding, and Interactions with Extracellular Matrix by Nonpeptidic Mimetics of Arg-Gly-Asp", pp. 1030-1036.

D. Cox, Drug News & Perspectives, 1995, 8, "Integrin antagonists are a new challenge to the pharmaceutical industry and their development will require a multidisciplinary approach, with scientists from different areas working together. Targets in Integrin Research", pp. 197-205.

J. Rico et al., J. Org. Chem, 1993, 58, "A Highly Steroselective Michael Addition to an $\alpha,\beta$-Unsaturated Ester as the Crucial Step in the Synthesis of a Novel $\beta$-Amino Acid-Containing Fibrinogen Receptor Antagonist", pp. 7948-7951.

C. H. Senanayake et al., Tetrahedron Lett., 1999, 40, "Properly tuned first fluoride-catalyzed TGME-mediated amination process for chloroimidazoles: inexpensive technology for antihistaminic norastemizole" pp. 6875-6879.

R. M. Keenan et al., Bioorg. Med. Chem. Lett., 1998, 8, "Discovery Of An Imidazopyridine-Containing 1,4-Benzodiazepine Nonpeptide Vitronnectin Receptor ($\alpha v\beta 3$) Antagonist With Efficacy In A Restenosis Model", pp. 3171-3176.

J.V. Greenhill et al., Chem. Soc., Perkin Trans. 2, 1985 (8), "Conformational and Tautomeric Studies of Acylguanidines. Part 1. Synthesis, Ultraviolet Spectroscopy, Tautomeric Preference, and Site of Protonation in Some Model Compounds", pp. 1255-1264.

C. Gilon et al., Tetrahedron, 1967, 23, "Synthesis of $\omega$-Aminooxy Acids by Oxygen-Alkyl fission of Lactones", pp. 4441-4447.

B.J. Ludwig et al., J. Med. Chem., 1970, 13, "Synthesis and Hypoglycemic Activity of Substituted Alkyl- and Alkoxyguanidines", pp. 60-63.

R.J. Mehta et al, Biochem J., 1998, 330, "Transmembrance-truncated $\alpha v\beta 3$ integrin retains high affinity for ligand binding: evidence for an 'inside-out' suppresor?", pp. 861-869.

Biorganic & Medicinal Chemistry Letters, vol. 6, No. 20, pp. 2372-2376, 1996—Solid-Phase Parallel Synthesis Applied to Lead Optimization: Discovery of Potent Analogues of the GPIIb/IIIa Antagonist RWJ-50042.

Clinical Exp. Immunol. 1994: vol. 95, pp. 270-276—"Inhibition of CD4+T lymphocyte binding to fibronectin and immune-cell accumulation in inflammatory sites by non-peptidic mimetics of arg-Gly-Asp" by R. Hershkovitz, N. Greenspoon, Y.A. Mekoris, P. Hadaris, R. Alon, G. Kapustina & O. Lider.

Varon, David et al., "Inhibition of Integrin-Mediated Platelet Aggregation, Fibrinogen-Binding, and interactions with Extracellular Matrix by Nonpeptidic Mimetics of Arg-Gly-Asp", Thrombosis and Haemostasis 1993 (70(6), pp. 1030-1036, XP-000979521.

Su, Ting et al., "Fibrinogen Receptor (GPIIb-IIIa) Antagonists Derived from 5, 6-Bicyclic Templates. Amidinoindoles, Amidinoindazoles, and Amidinobenzofurans Containing the N-alpha-Sulfonamide Carboxylic Acid Function as Potent Platelet Aggregation Inhibitors", J. Med. Chem 1997 40(26), pp. 4308-4318, XP-000915289.

Hosoda, Akihiko et al., "Preparation to N-(heterocyclyicarbonyl)amino Acids and Analogs as Prolyl Endopeptidase Inhibitors", Chemical Abstracts, vol. 118, No. 25, Jun. 21, 1993, Columbus, Ohio, XP-002159418.

Archelos, J.J., "The role of integrins in immune-mediated diseases of the nervous system", TNS, vol. 22, No. 1, 1999, pp. 30-38.

Cotman. C.W.. et al., "Cell Adhesion Molecules in Neural Plasticity and Pathology: Similar Mechanisms, Distinct Organizations?", Progress in Neurobiology. vol. 55, 1998, pp. 659-669.

Milner, R., "Understanding the molecular basis of cell migration; implications for clinical therapy in multiple sclerosis", Clinical Science, (1997) 92, pp. 113-122.

Fossati, G., et al., In vitro effects of GM-CSF on mature peripheral blood neutrophils, International Journal of Molecular Medicine 1, 1998, pp. 943-951.

Hynes, R.O., "Integrins: Versatility, Modulation, and Signaling in Cell Adhesion", Cell. vol. 69, Apr. 3, 1992, pp. 11-25.

Lee, J., et al., Crystal Structure of the A Domain from the $\alpha$ Subunit of Integrin CR3 (CD11b/CD18); Cell, vol. 80, Feb. 24, 1995, pp. 631-638.

McCoy, L.E., "Basic Concepts of Hemostasis and thrombosis: Clinical and Laboratory Evaluation of Thrombohemorrhagic Phenomena", Murano, G., Bick, R.L. Eds.; CRC: Boca Raton, Florida, 1980, pp. 5-15.

Hughes, P.E., et al., "Integrin affinity modulation", Trends in Cell Biology, 1998, vol. 8, pp. 359-364.

Clover, J., et al., "Integrin subunit expression by human osteoblasts and osteoclasts in situ and in culture" Journal of Cell Science, 103, pp. 267-271.

Duggan, M.E., et al., "Nonpeptide of $\alpha_v\beta_3$ Antagonists. 1. Transformation of a Potent, Integrin-Selective $\alpha_{IIb}\beta_3$ Antagonist into a Potent $\alpha_v\beta_3$ Antagonist" J. Med. Chem, 2000, 43, pp. 3736-3745.

Attur, Mukundan G., "Functional Genomic Analysis in Arthritis-Affected Cartilage: Yin-Yang Regulation of Inflammatory Mediators by $\alpha_5\beta_1$ and $\alpha_v\beta_3$ Integrins", The Journal of Immunogoly, Copyright 2000 by The american Association of Immunologists, pp. 2684-2691.

Buckley, C.D., "Identification of $\alpha_v\beta_3$ as a heterotypic ligand for CD31/PECAM-1", Journal of Cell Science, 109, 1996, pp. 437-445.

Scaffidi, Amelia K., "Regulation of human lung fibroblast phenotype and function by vitronectin and vitronectin integrins", Journal of Cell Science, 114, 2001, pp. 3507-3516.

Fields, Gregg B., "Integrins: cell adhesion molecules in cancer", Exp. Opin. Ther. Patents (1998), 8(6), pp. 633-644.

Byzova, Tatiana V., et al., "Role of Integrin $\alpha_v\beta_3$ in Vascular Biology", Thromb. Haemost, (1998), 80, pp. 726-734.

Larksarp, Chitchamai et al., "Palladium-Catalyzed Cyclocarbonylation of o-Iodoanilines with Heterocumulenes: Regioselective Preparation of 4(3H)-Quinazolinone Derivatives", J. Org. Chem. 2000, 65, pp. 2773-2777.

PCT International Search Report dated Feb. 24, 2001 for PCT Appln. No. PCT/US00/26163, which is related to U.S. Appl. No. 09/667,134.

Communication for the European Patent Office dated Jan. 16, 2002, for European Patent Application No. 00 966 823.7-2117.

* cited by examiner

ISONIPECOTAMIDES FOR THE TREATMENT OF INTEGRIN-MEDIATED DISORDERS

CROSS-REFERENCE TO RELATED APPLICATIONS

This application is a continuation of Ser. No. 09/667,134 filed Sep. 21, 2000 now abandoned and claims the benefit of Ser. No. 60/156,617 filed Sep. 29, 1999.

FIELD OF THE INVENTION

This invention relates to certain novel compounds, their synthesis and methods for their use in treating integrin-mediated disorders. More particularly, this invention relates to isonipecotamide compounds that are αvβ3, αvβ5, GPIIb/IIIa, dual αvβ3/GPIIb/IIIa or dual αvβ3/αvβ5 integrin antagonists and methods for their use in treating a variety of integrin-mediated disorders.

BACKGROUND OF THE INVENTION

Integrins are a widely expressed family of calcium- or magnesium-dependent αβ heterodimeric cell surface receptors which bind to extracellular matrix adhesive proteins such as fibrinogen, fibronectin, vitronectin, and osteopontin. These transmembrane glycoproteins (GP's), known for their large extracellular domains, are classified by at least 8 known β subunits and 14 α subunits (S. A. Mousa, et al., *Emerging Theraupeutic Targets*, 2000, 4, (2), 143-153). For example, the β1 subfamily, also known as the very late antigen (VLA) subfamily, has the largest number of integrins (S. A. Mousa, et al., *Emerging Theraupeutic Targets*, 2000, 4, (2), 144). The αvβ1 subfamily further associates with various β subunits: β3, β5, β6, β8 and αIIbβ3 (also referred to as GPIIb/IIIa) (S. A. Mousa, et al., *Emerging Theraupeutic Targets*, 2000, 4, (2), 144, 147). Some of the disease states that have a strong β3, β5 and GPIIb/IIIa integrin component in their etiologies are unstable angina, thromboembolic disorders or atherosclerosis (GPIIb/IIIa); thrombosis or restenosis (GPIIb/IIIa or αvβ3); restenosis (dual αvβ3/GPIIb/IIIa); rheumatoid arthritis, vascular disorders or osteoporosis (αvβ3); tumor angiogenesis, multiple sclerosis, neurological disorders, asthma, vascular injury or diabetic retinopathy (αvβ3 or αvβ5); and, angiogenesis (dual αvβ3/αvβ5) (S. A. Mousa, et al., *Emerging Theraupeutic Targets*, 2000, 4, (2), 148-149; W. H. Miller, et al., *Drug Discovery Today* 2000, 5 (9), 397-407; and, S. A. Mousa, et al., *Exp. Opin. Ther. Patents*, 1999, 9 (9), 1237-1248). The β3 subunit has received significant attention in recent drug discovery efforts. (W. J. Hoekstra, *Current Medicinal Chemistry* 1998, 5, 195) and antibodies and/or low-molecular weight compound antagonists of αvβ3 have shown efficacy in animal models (J. Samanen, *Current Pharmaceutical Design* 1997, 3, 545).

Furthermore, GPIIb/IIIa and αvβ3 antagonists have typically been designed after the bioactive arginine-glycine-aspartate (RGD) conformations of peptides derived from their primary ligands, fibrinogen and vitronectin, respectively. The RGD motif is the general cell attachment sequence of many extracellular matrix, blood, and cell surface proteins, as half of the ca. 20 known integrins bind the RGD-containing adhesion ligands. To discover RGD peptides with integrin selectivity, peptides with both restricted conformations and alterations of flanking residues have been studied. In particular, the structural requirements for interaction of the RGD sequence with GPIIb/IIIa and the inhibitory potential of a series of nonpeptidic mimetics on platelet aggregation and interactions with the extracellular matrix have been described (D. Varon, et al., *Thromb. Haemostasis*, 1993, 70(6), 1030-1036). Iterative synthesis of cyclic and alicyclic peptides and computer modelling have provided potent, selective agents as a platform for nonpeptide αv integrin antagonist design.

For example, PCT Application WO98/25892 to Fisher, et al., describes a series of α-sulfonamido and α-sulfinamido carboxylic acid compounds of the formula:

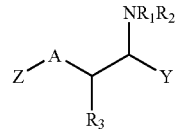

wherein
Y is selected from the group consisting of —COOH, —PO$_3$H$_2$, —SO$_3$H and —COOR$^4$; where R4 is selected from the group consisting of C$_{1-10}$alkyl,
C$_{1-8}$alkylaryl, arylC$_{1-8}$alkyl, C$_{1-8}$alkyloxycarbonyloxyC$_{1-8}$alkyl,
aryloxycarbonyloxyC$_{1-8}$alkyl, C$_{1-8}$alkyloxycarbonyloxyaryl,
C$_{1-10}$alkylcarbonyloxyC$_{1-8}$alkyl and C$_{1-8}$alkylcarbonyloxyaryl; A is selected from the group consisting of C$_{6-12}$alkyl, C$_{0-8}$alkyl-NR$^5$—CO—C$_{0-8}$alkyl,
C$_{0-8}$alkyl-CO—NR$^5$—C$_{0-8}$alkyl, C$_{0-8}$alkyl-O—C$_{0-8}$alkyl,
C$_{0-8}$alkyl-NR$^5$—CO—C$_{1-8}$alkyl-NR$^5$—CO—C$_{0-8}$alkyl,
C$_{0-8}$alkyl-NR$^5$—CO—C$_{1-8}$alkyl-CO—NR$^5$—C$_{0-8}$alkyl,
C$_{0-8}$alkyl-CO—NR$^5$—C$_{1-8}$alkyl-NR$^5$—CO—C$_{0-8}$alkyl,
C$_{0-8}$alkyl-CO—NR$^5$—C$_{0-8}$alkyl-CO—N R$^5$—C$_{0-8}$alkyl,
C$_{0-8}$alkyl-CO—C$_{1-8}$alkyl-CO—NR$^5$—C$_{0-8}$alkyl,
C$_{0-8}$alkyl-CO—C$_{0-8}$alkyl-NR$^5$—CO—CO$_{0-8}$alkyl,
C$_{0-8}$alkyl-O—C$_{2-8}$alkyl-NR$^5$—CO—C$_{0-8}$alkyl,
C$_{0-8}$alkyl-O—C$_{0-8}$alkyl-CO—NR$^5$—C$_{0-8}$alkyl,
C$_{0-8}$alkyl-O—C$_{2-8}$alkyl-O—C$_{0-8}$alkyl-CO—NR$^5$—C$_{0-8}$alkyl, C$_{0-8}$alkyl-S—C$_{0-8}$alkyl,
C$_{0-8}$alkyl-S(O$_n$)—C$_{0-8}$alkyl, C$_{0-8}$alkyl-S—C$_{2-8}$alkyl-NR$^5$—CO—C$_{0-8}$alkyl,
C$_{0-8}$alkyl-S(O$_n$)—C$_{2-8}$alkyl-NR$^5$—CO—C$_{0-8}$alkyl,
C$_{0-8}$alkyl-S—C$_{0-8}$alkyl-CO—NR$^5$—C$_{0-8}$alkyl,
C$_{0-8}$alkyl-S(O$_n$)—C$_{1-8}$alkyl-CO—NR$^5$—C$_{0-8}$alkyl,
C$_{0-8}$alkyl-NR$^5$—CO—C$_{0-8}$alkyl-S—C$_{0-8}$alkyl,
C$_{0-8}$alkyl-NR$^5$—CO—C$_{1-8}$alkyl-S(O$_n$)—C$_{0-8}$alkyl,
C$_{0-8}$alkyl-CO—NR$^5$—C$_{2-8}$alkyl-S—C$_{0-8}$alkyl,
C$_{0-8}$alkyl-CO—NR$^5$—C$_{2-8}$alkyl-S(O$_n$)—C$_{0-8}$alkyl,
C$_{0-8}$alkyl-NR$^5$—C$_{0-8}$alkyl-CO$_2$—C$_{0-8}$alkyl, C$_{0-8}$alkyl-NR$^5$—C$_{0-8}$alkyl-CS—O—C$_{0-8}$alkyl,
C$_{0-8}$alkyl-NR$^5$—C$_{0-8}$alkyl-CO—NR$^5$—C$_{0-8}$alkyl,
C$_{0-8}$alkyl-NR$^5$—C$_{0-8}$alkyl-CS—NR$^5$—C$_{0-8}$alkyl, C$_{0-8}$alkyl-O—C$_{0-8}$alkyl-CO$_2$-C$_{0-8}$alkyl,
C$_{0-8}$alkyl-O—C$_{0-8}$alkyl-CS—O—C$_{0-8}$alkyl, C$_{0-8}$alkyl-SiR$^7$R$^8$—C$_{0-8}$alkyl,
C$_{0-8}$alkyl-SiR$^7$R$^8$—C$_{0-8}$alkyl-NR$^6$—CO—C$_{0-8}$alkyl and
C$_{0-8}$alkyl-SiR$^7$R$^8$—C$_{0-8}$alkyl-CO—NR$^6$—C$_{0-8}$alkyl; where R$^5$, R$^6$, R$^7$ and R$^8$— are independently selected from the group consisting of H and C$_{1-6}$alkyl; and where
n=1 or 2; Z is selected from the group consisting of —NH—C(NR$^9$R$^{10}$)=R$^{11}$, —NH—C(R$^9$)=R$^{11}$, —C(NR$^9$R$^{10}$)=R$^{11}$ and piperidinyl; where R$^9$, R$^{10}$ and R$^{11}$ are independently selected from the group consisting of H, C$_{1-6}$alkyl, arylC$_{1-3}$alkyl and aryl; or where two of the R$^9$, R$^{10}$ or R$^{11}$ substituents form a cyclic ring containing (CH$_2$)$_p$, where p=2-5; R$_1$ is H and R$_2$ is selected from the group consisting of —SO$_m$- aryl-, —SO$_m$—C$_{1-10}$alkyl-, —SO$_m$-heteroaryl-, where m=1-2; R$^3$ is selected from the group consisting of H, C$_{1-8}$alkyl, aryl, C$_{1-8}$alkylaryl and heteroaryl as inhibitors of RGD-dependent integrins for the treatment of thrombotic or restenotic disorders.

Accordingly, it is an object of the present invention to provide compounds that are antagonists of integrins. It is another object to provide isonipecotamide compounds that are αvβ3, αvβ5, GPIIb/IIIa, dual αvβ3/GPIIb/IIIa or dual αvβ3/αvβ5 integrin antagonists. It is a further object to provide methods for treating a variety of integrin-mediated disorders including, but not limited to, unstable angina, thromboembolic disorders, atherosclerosis, arterial and/or venous thrombosis, restenosis, rheumatoid arthritis, vaso-occlusive disorders, osteoporosis, tumor angiogenesis, multiple sclerosis, neurological disorders, asthma, vascular injury, macular degeneration or diabetic complications including diabetic retinopathy.

SUMMARY OF THE INVENTION

The present invention is directed to compounds represented by the following general Formula (I):

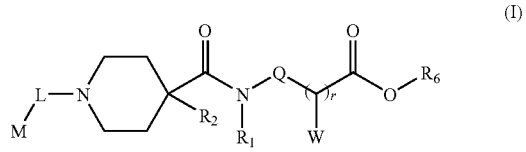

wherein

M is selected from C$_1$-C$_4$ alkylene (optionally substituted within the carbon chain with one substituent selected from C$_1$-C$_4$ alkyl, C$_2$-C$_4$ alkenyl, cycloalkyl (wherein a ring carbon atom forms the point of attachment to the carbon chain) or aryl (optionally substituted with halogen) and substituted on the terminal carbon with one substituent selected from A), C$_2$-C$_4$ alkenylene (substituted with one substituent selected from A), heterocyclylene (optionally substituted with one substituent selected from A), heterocyclenylene (substituted with one substituent selected from A), arylene (substituted with one substituent selected from A), (C$_1$-C$_4$ alkylene)aryl (substituted on C$_1$-C$_4$ alkylene with one substituent selected from A), cyclopent-2-enylene, or arylene(C$_1$-C$_4$)alkyl (substituted on arylene with one substituent selected from A);

A is optionally present and is selected from heteroaryl, heterocyclyl, R$_3$HN—,(heteroaryl)amino, (heterocyclyl)amino, R$_3$HNC(=NH)—, R$_3$HNC(=NH)NH—, R$_3$HNC(=O)NH—, R$_3$C(=NH)NH—, (heterocyclyl)aminooxy, (heteroaryl)aminooxy, R$_3$HNC(=NH)NHO—, R$_3$C(=NH)NHO—, R$_3$HNC(=NH)NHC(=O)— or R$_3$C(=NH)NHC(=O)—; wherein heteroaryl and heterocyclyl are optionally substituted with one to five substituents independently selected from C$_1$-C$_4$ alkyl, C$_1$-C$_4$ alkoxy, heteroaryl (optionally substituted with C$_1$-C$_4$ alkyl), halogen, hydroxy, nitro, cyano, trihalo(C$_1$-C$_4$)alkyl, C$_1$-C$_4$ alkylcarbonyl, C$_1$-C$_4$ alkoxycarbonyl, aryl(C$_1$-C$_4$)alkoxycarbonyl, R$_3$HN—, amino(C$_1$-C$_4$)alkyl, C$_1$-C$_4$ alkylamino(C$_1$-C$_4$)alkyl or di(C$_1$-C$_4$ alkyl)amino(C$_1$-C$_4$)alkyl;

with the proviso that if A is H$_2$NC(=NH)NH—, then, dependently, W is not hydrogen when Q is —CH$_2$—;

L is selected from —C(=O)—, —SO$_2$—, —OC(=O)— or —HNC(=O)—;

R$_1$ is selected from hydrogen, C$_1$-C$_8$ alkyl or cycloalkyl;

R$_2$ is selected from hydrogen or C$_1$-C$_8$ alkyl;

R$_3$ is selected from hydrogen, C$_1$-C$_8$ alkyl, aryl, aryl(C$_1$-C$_8$) alkyl, cycloalkyl, hydroxy, cyano or nitro;

Q is selected from —CH$_2$—, —CH(C$_1$-C$_8$alkyl)-, —CH(C$_2$-C$_8$alkenyl)-, —CH(C$_2$-C$_8$alkynyl)-, —CH(aryl)- (wherein aryl is optionally substituted with one to five substituents independently selected from C$_1$-C$_4$ alkyl, C$_1$-C$_4$ alkoxy, —O—(C$_1$-C$_3$ alkyl)-O—, halogen, hydroxy, trihalo(C$_1$-C$_3$)alkyl or trihalo(C$_1$-C$_3$)alkoxy), —CH(heteroaryl)- (wherein heteroaryl is optionally substituted with a substituent selected from halogen, hydroxy, C$_1$-C$_4$ alkyl, C$_1$-C$_4$ alkoxy, —O—(C$_1$-C$_3$ alkyl)-O—, amino, C$_1$-C$_4$ alkylamino or di(C$_1$-C$_4$)alkylamino) or —CH(aryl(C$_1$-C$_8$) alkyl)-;

W is selected from hydrogen or N(R$_4$)T;

r is an integer selected from 0 or 1;

R$_4$ is selected from hydrogen, C$_1$-C$_8$ alkyl or C$_2$-C$_6$ acyl;

T is selected from R$_5$C(=O)—, R$_5$OC(=O)— or R$_5$C(=N—CN)—;

R$_5$ is selected from C$_1$-C$_8$ alkyl, aryl, aryl(C$_1$-C$_8$)alkyl or amino (wherein amino is optionally substituted with one to two substituents independently selected from C$_1$-C$_8$ alkyl);

R$_6$ is selected from hydrogen, C$_1$-C$_8$ alkyl, aryl(C$_1$-C$_8$)alkyl, (R$_7$)N(C$_1$-C$_8$)alkyl, (R$_8$)(R$_7$)N(C$_1$-C$_8$)alkyl or (R$_8$)(R$_7$)NC(=O)(C$_1$-C$_8$)alkyl; and, R$_7$ and R$_8$ are independently selected from hydrogen, C$_1$-C$_8$ alkyl or cycloalkyl;

and pharmaceutically acceptable salts thereof.

Illustrative of the invention is a pharmaceutical composition comprising a pharmaceutically acceptable carrier and any of the compounds described above. Illustrating the invention is a pharmaceutical composition made by mixing any of the compounds described above and a pharmaceutically acceptable carrier. An illustration of the invention is a process for making a pharmaceutical composition comprising mixing any of the compounds described above and a pharmaceutically acceptable carrier.

An example of the invention is a method of treating integrin-mediated disorders in a subject in need thereof comprising administering to the subject a therapeutically effective amount of any of the compounds or pharmaceutical compositions described above. Examples of integrin-mediated disorders include, but are not limited to, unstable angina, thromboembolic disorders, atherosclerosis, arterial and/or venous thrombosis, restenosis, rheumatoid arthritis, vaso-occlusive disorders, osteoporosis, tumor angiogenesis, multiple sclerosis, neurological disorders, asthma, vascular injury, macular degeneration or diabetic complications, including diabetic retinopathy.

Further exemplifying the invention is the method of treating integrin-mediated disorders, wherein the therapeutically effective amount of the compound is from about 0.01 mg/kg/day to about 300 mg/kg/day.

Also included in the invention is the use of a compound of Formula (I) for the preparation of a medicament for treating an integrin-mediated disorder in a subject in need thereof.

The isonipecotamide compounds of the present invention are integrin antagonists; particularly, αvβ3, αvβ5, GPIIb/IIIa, dual αvβ3/GPIIb/IIIa and dual αvβ3/αvβ5 integrin antagonists. The instant compounds are useful in treating thrombotic disorders such as restenosis, arterial and venous thrombosis, acute myocardial infarction, re-occlusion following thrombolytic therapy and angioplasty, inflammation, unstable angina, atherosclerosis, angiogenesis and a variety of vaso-occlusive disorders. These compounds are also useful as antithrombotics used in conjunction with fibrinolytic therapy (e.g., t-PA or streptokinase). Additionally, the compounds are useful in treating and preventing osteoporosis, rheumatoid arthritis, bone resorption, cancer, macular degeneration, and diabetic complications including diabetic retinopathy.

DETAILED DESCRIPTION OF THE INVENTION

Relative to the above generic description, certain compounds of Formula (I) are preferred.

The preferred embodiments of the present invention are those compounds wherein, independently, M is selected from ethylene (optionally substituted within the carbon chain with methyl and substituted on the terminal carbon with one substituent selected from A), propylene (optionally substituted within the carbon chain with methyl, ethenyl, cyclohexylidene [wherein a ring carbon atom forms the point of attachment to the carbon chain] or 4-Cl-phenyl and substituted on the terminal carbon with one substituent selected from A), allylene (substituted with one substituent selected from A); piperidin-4-ylene (optionally substituted with one substituent selected from A), cyclopent-2-en-1-ylene (substituted with one substituent selected from A) or 4-methylenephenyl (substituted on methylene with one substituent selected from A);

A is optionally present and is selected from 1H-imidazol-1-yl, 1H-imidazol-2-yl, 4,5-dihydro-1H-imidazol-2-yl (optionally substituted with a substituent selected from $C_1$-$C_4$ alkoxycarbonyl or aryl($C_1$-$C_4$)alkoxycarbonyl), pyridin-2-yl (optionally substituted with a substituent selected from $C_1$-$C_4$ alkyl, heteroaryl [optionally substituted with $C_1$-$C_4$ alkyl], halogen, hydroxy, nitro, cyano, amino, amino($C_1$-$C_4$)alkyl, $C_1$-$C_4$ alkylamino(Cl-$C_4$)alkyl or di($C_1$-$C_4$ alkyl)amino($C_1$-$C_4$)alkyl), pyrimidin-2-yl, 1,4,5,6-tetrahydro-pyrimidin-2-yl (optionally substituted with one to two substituents independently selected from $C_1$-$C_4$ alkyl, hydroxy or amino), piperidin-4-yl, benzimidazol-2-yl, 1,2,3,4-tetrahydro-1,8-naphthyridin-7-yl, 3H-imidazo[4,5-b]pyridin-2-yl, amino, ($C_1$-$C_6$ alkyl)amino, (1H-imidazol-1-yl)amino, (1H-imidazol-2-yl)amino, (4,5-dihydro-1H-imidazol-2-yl)amino (optionally substituted on 4,5-dihydro-1H-imidazol-2-yl with a substituent selected from $C_1$-$C_6$ alkoxycarbonyl or aryl($C_1$-$C_6$)alkoxycarbonyl), (pyridin-2-yl)amino (optionally substituted on pyridin-2-yl with a substituent selected from $C_1$-$C_4$ alkyl, heteroaryl [optionally substituted with $C_1$-$C_4$ alkyl], halogen, hydroxy, nitro, cyano, amino, amino($C_1$-$C_4$)alkyl, $C_1$-$C_4$ alkylamino($C_1$-$C_4$)alkyl or di($C_1$-$C_4$ alkyl)amino($C_1$-$C_4$)alkyl), (pyrimidin-2-yl)amino, (1,4,5,6-tetrahydro-pyrimidin-2-yl)amino (optionally substituted on 1,4,5,6-tetrahydro-pyrimidin-2-yl with one to two substituents independently selected from $C_1$-$C_4$ alkyl, hydroxy or amino), (4,5,6,7-tetrahydro-1H-1,3-diazepin-2-yl)amino, (thiazol-2-yl)amino, (benzimidazol-2-yl)amino, (3H-imidazo[4,5-b]pyridin-2-yl)amino, $R_3$HNC(=NH)NH—, $R_3$HNC(=O)NH—, (4,5,6,7-tetrahydro-1H-1,3-diazepin-2-yl)aminooxy, (4,5-dihydro-1H-imidazol-2-yl)aminooxy or $R_3$HNC(=NH)NHO—;

more preferably, A is optionally present and is selected from 1H-imidazol-1-yl, 4,5-dihydro-1H-imidazol-2-yl, pyridin-2-yl (optionally substituted with a substituent selected from $C_1$-$C_4$ alkyl or heteroaryl [optionally substituted with $C_1$-$C_4$ alkyl]), piperidin-4-yl, benzimidazol-2-yl, 1,2,3,4-tetrahydro-1,8-naphthyridin-7-yl, 3H-imidazo[4,5-b]pyridin-2-yl, amino, (4,5-dihydro-1H-imidazol-2-yl)amino (optionally substituted on 4,5-dihydro-1H-imidazol-2-yl with $C_1$-$C_6$ alkoxycarbonyl), (pyridin-2-yl)amino (optionally substituted on pyridinyl with a substituent selected from $C_1$-$C_4$ alkyl or heteroaryl [optionally substituted with $C_1$-$C_4$ alkyl]), (1,4,5,6-tetrahydro-5-hydroxypyrimidin-2-yl)amino, (1,4,5,6-tetrahydro-5-methylpyrimidin-2-yl)amino, (1,4,5,6-tetrahydro-5,5-dimethylpyrimidin-2-yl)amino, (thiazol-2-yl)amino, (3H-imidazo[4,5-b]pyridin-2-yl)amino, $R_3$HNC(=NH)NH—, $R_3$HNC(=O)NH—, (4,5-dihydro-1H-imidazol-2-yl)aminooxy or $R_3$HNC(=NH)NHO—;

most preferably, A is optionally present and is selected from 4,5-dihydro-1H-imidazol-2-yl, 1,2,3,4-tetrahydro-1,8-naphthyridin-7-yl, 3H-imidazo[4,5-b]pyridin-2-yl, amino, (4,5-dihydro-1H-imidazol-2-yl)amino, (pyridin-2-yl)amino, (3-methylpyridin-2-yl)amino, (thiazol-2-yl)amino, (3H-imidazo[4,5-b]pyridin-2-yl)amino, $NH_2$C(=NH)NH—, $R_3$HNC(=O)NH—, (4,5-dihydro-1H-imidazol-2-yl)aminoxy or $NH_2$C(=NH)NHO—, with the proviso that if A is $H_2$NC(=NH)NH—, then, dependently, W is not hydrogen when Q is —$CH_2$—;

L is selected from —C(=O)—, —OC(=O)— or —HNC(=O)—;

$R_1$ is selected from hydrogen or $C_1$-$C_4$ alkyl; more preferably, $R_1$ is hydrogen;

$R_2$ is hydrogen;

$R_3$ is selected from hydrogen, $C_1$-$C_8$ alkyl, aryl($C_1$-$C_8$)alkyl or hydroxy; more preferably, $R_3$ is selected from hydrogen, butyl, benzyl or hydroxy;

Q is selected from —$CH_2$—, —CH($C_1$-$C_8$alkyl)-, —CH(aryl)- (wherein aryl is optionally substituted with one to five substituents independently selected from $C_1$-$C_4$ alkyl, $C_1$-$C_4$ alkoxy, —O—($C_1$-$C_3$ alkyl)-O—, halogen, hydroxy or trihalo($C_1$-$C_3$)alkyl), —CH(heteroaryl)- (wherein heteroaryl is optionally substituted with a substituent selected from halogen) or —CH(aryl($C_1$-$C_8$)alkyl)-;

more preferably, Q is selected from —$CH_2$—, —CH(methyl)-, —CH(ethyl)-, —CH(phenyl)- (wherein phenyl is optionally substituted with one to five substituents independently selected from methyl, ethyl, propyl, methoxy, ethoxy, propoxy, bromine, chlorine, fluorine, iodine, hydroxy or trifluoromethyl), —CH(naphthalen-1-yl)-, —CH(naphthalen-2-yl)-, —CH[(3,4-dioxymethylene)phenyl]-, —CH [(3,4-dioxyethylene)phenyl]-, —CH[(3-bromo-5-chloro-2-hydroxy)phenyl]-, —CH(thien-3-yl)-, —CH(quinolin-3-yl)-, —CH(pyridin-3-yl)- (wherein pyridinyl is optionally substituted with chlorine) or —CH(benzyl)-;

most preferably, 0 is selected from —$CH_2$—, —CH(methyl)-, —CH(phenyl)- (wherein phenyl is optionally substituted with one to five substituents independently selected from methyl, methoxy, bromine, chlorine, fluorine, hydroxy or trifluoromethyl), —CH(naphthalen-1-yl)-, —CH(naphthalen-2-yl)-, —CH [(3,4-dioxymethylene)phenyl]-, —CH[(3,4-dioxyethylene)phenyl]-, —CH [(3-bromo-5-chloro-2-hydroxy)phenyl]-, —CH(thien-3-yl)-, —CH(quinolin-3-yl)-, —CH(pyridin-3-yl)- (wherein pyridinyl is optionally substituted with chlorine) or —CH(benzyl)-;

r is 1;

$R_4$ is selected from hydrogen or $C_1$-$C_4$ alkyl;

more preferably, $R_4$ is hydrogen;

T is selected from $R_5$C(=O)— or $R_5$OC(=O)—;

more preferably, T is selected from $R_5$OC(=O)—;

$R_5$ is selected from aryl or aryl($C_1$-$C_4$)alkyl;

more preferably, $R_5$ is selected from aryl($C_1$-$C_4$)alkyl;

most preferably, $R_5$ is benzyl;

$R_6$ is selected from hydrogen, methyl or $(R_8)(R_7)NC(=O)CH_2$;
more preferably, $R_6$ is hydrogen;
$R_7$ and $R_8$ are independently selected from hydrogen, methyl or ethyl; and,
more preferably, $R_7$ and $R_8$ are independently ethyl;
and pharmaceutically acceptable salts thereof.
Exemplifying the invention is a compound of Formula (I) selected from:
1
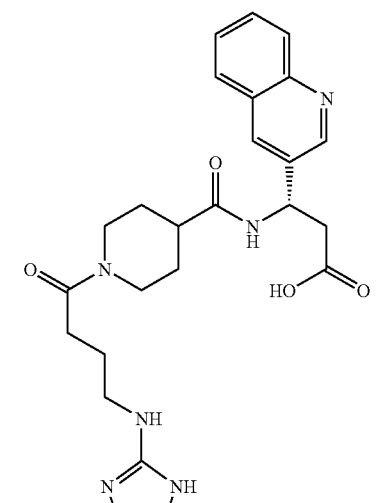
2
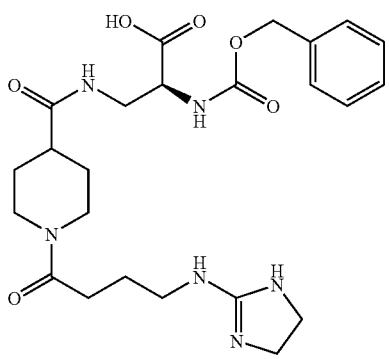
3
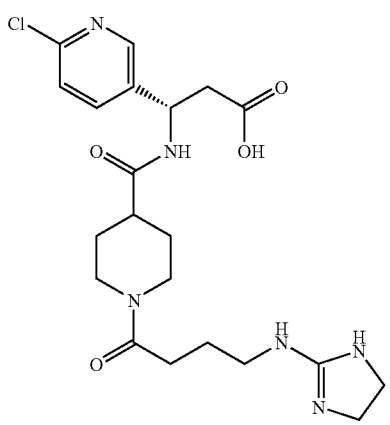
-continued
4
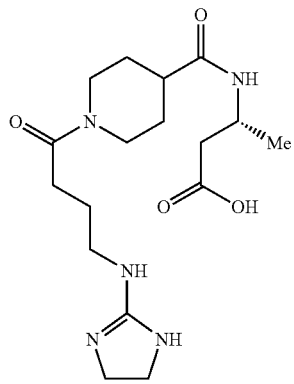
5
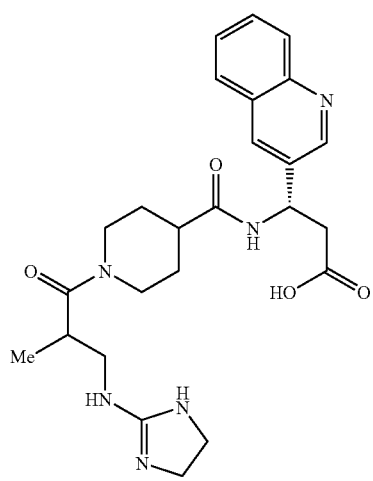
6
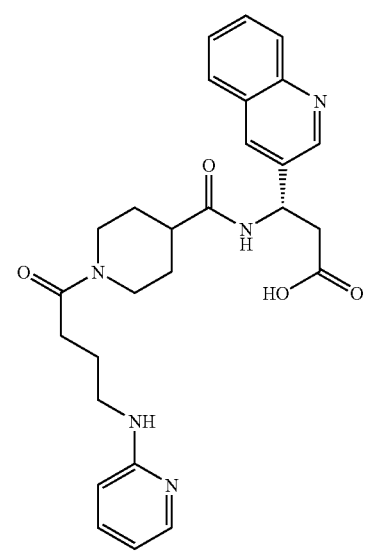

7
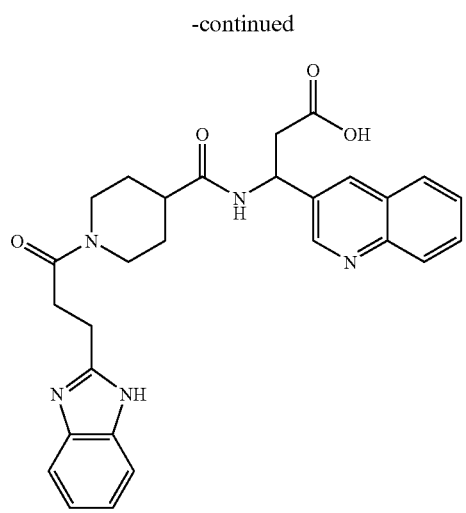
8
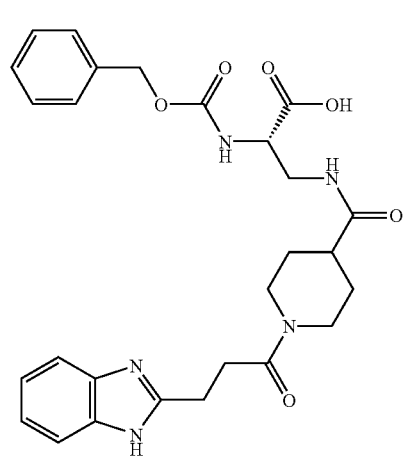
9
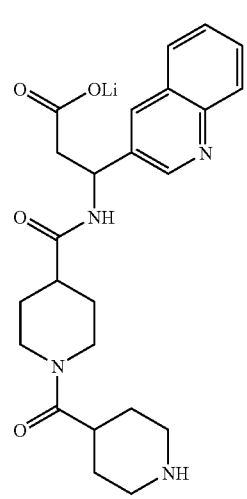
10
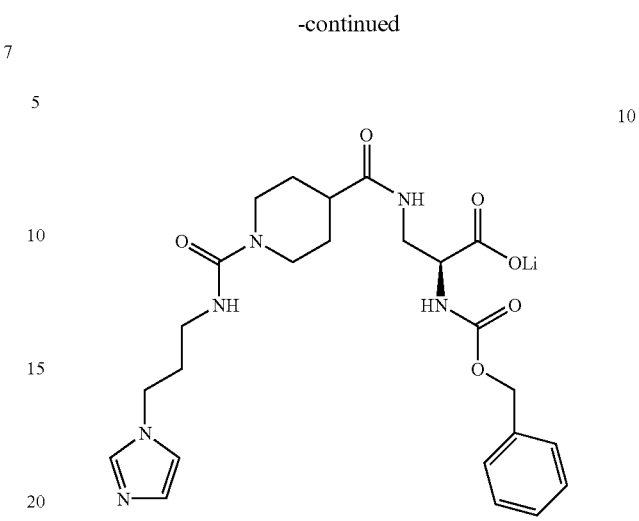
11
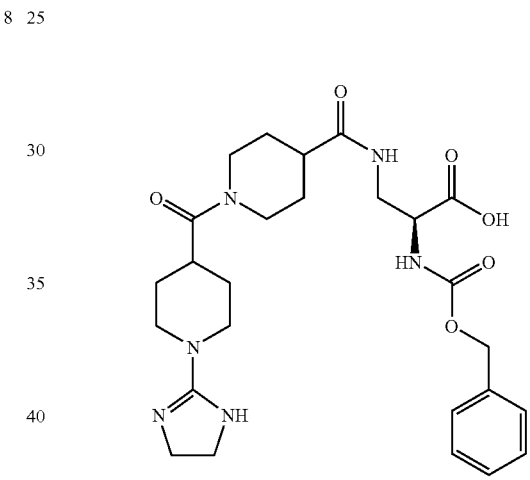
12
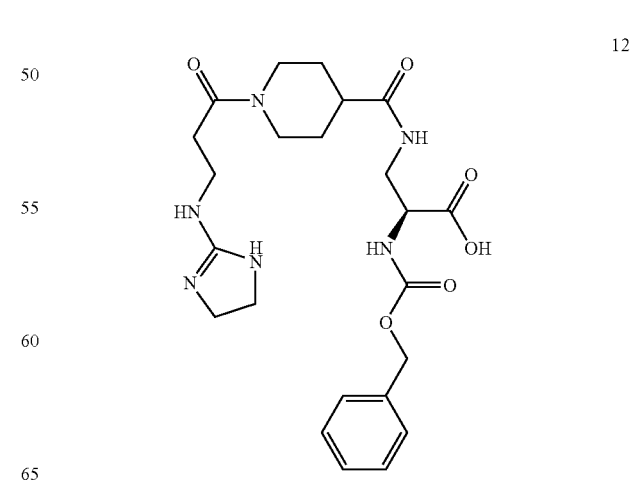

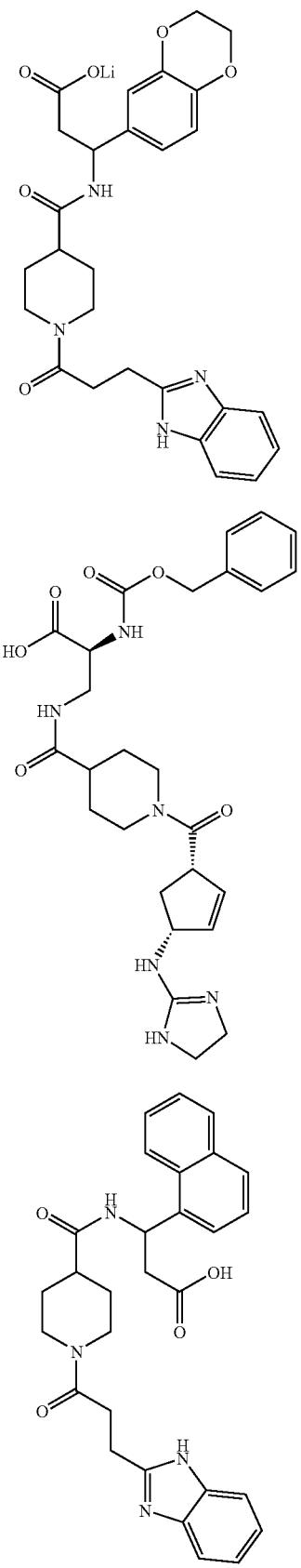
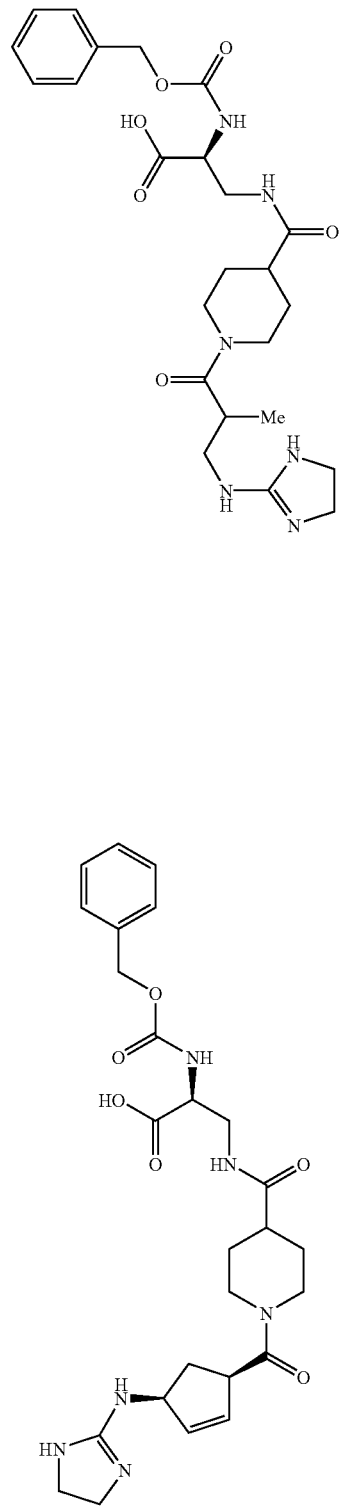

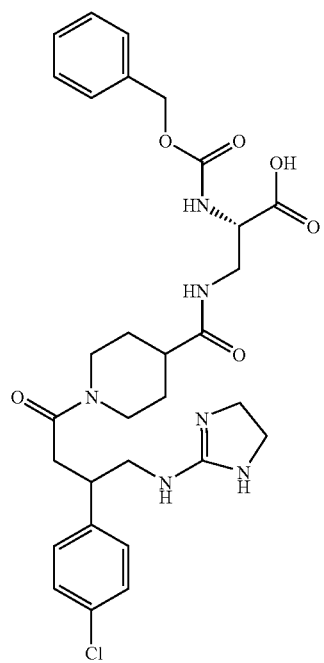
18
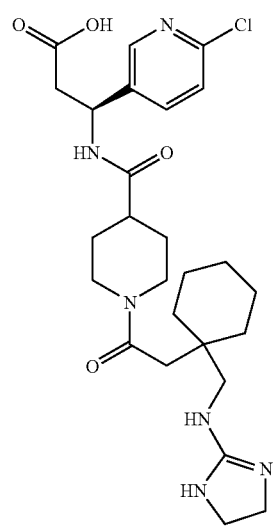
19
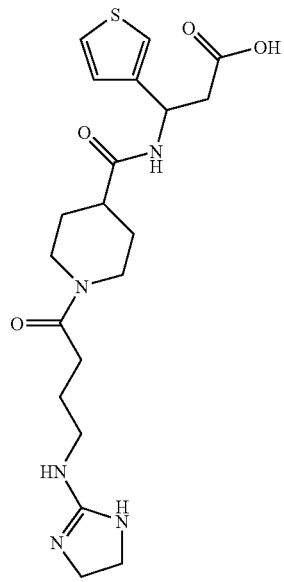
20
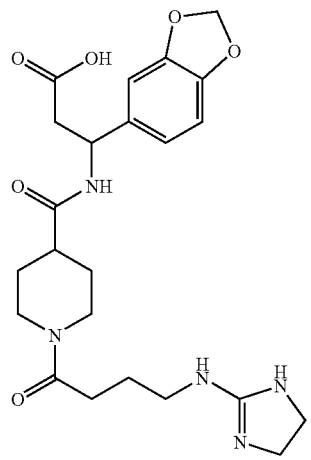
21
22

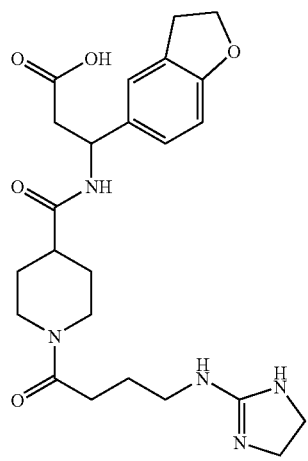
23
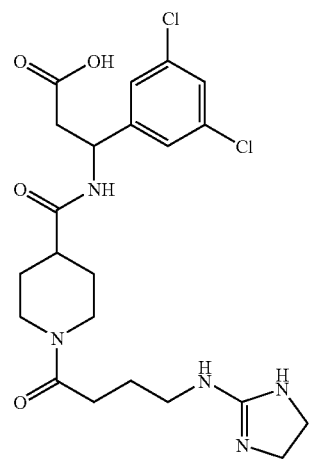
26
24
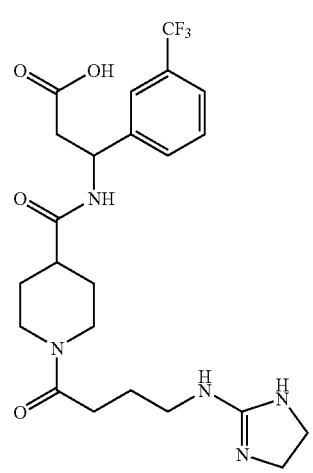
27
25
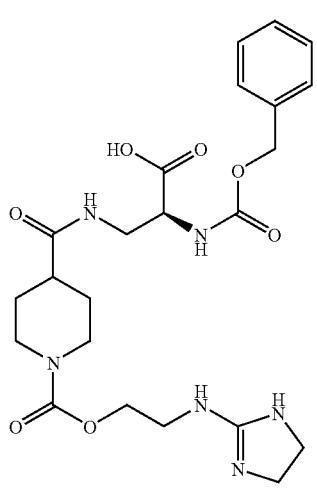
28

29
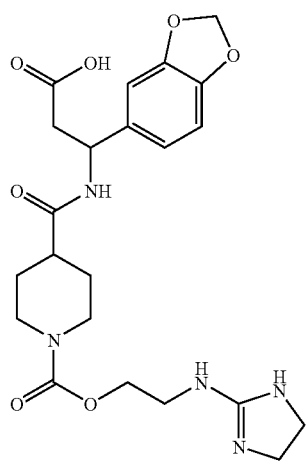
30
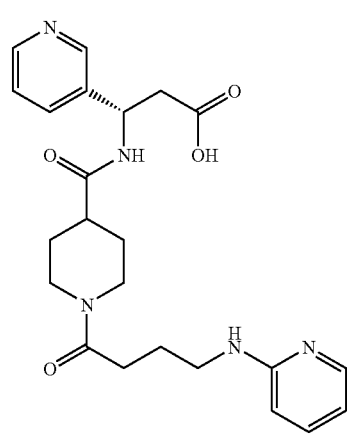
31
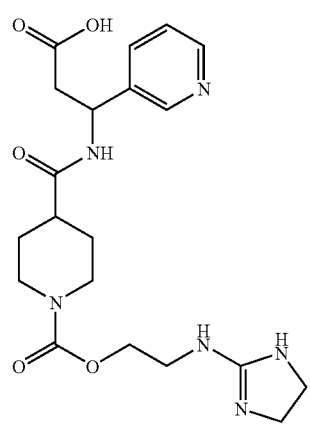
32
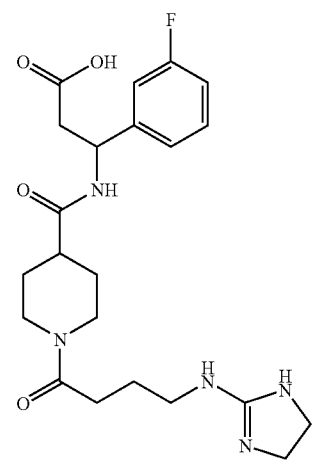
33
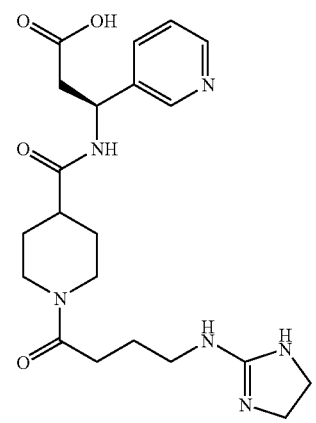
34
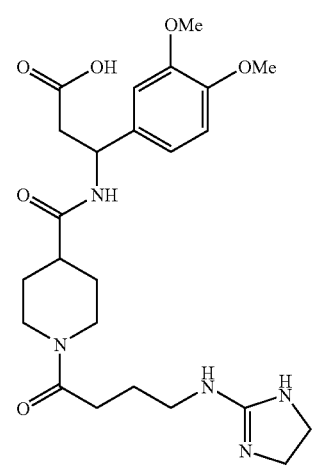

35 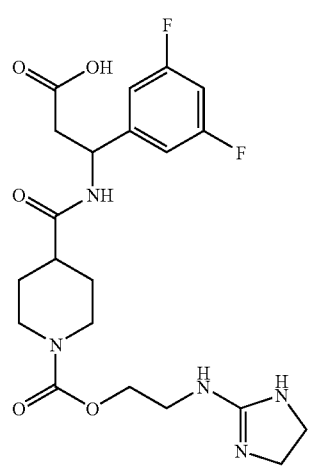
36 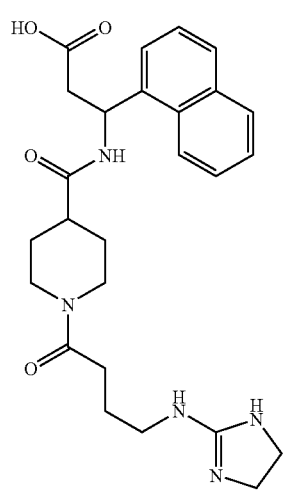
37 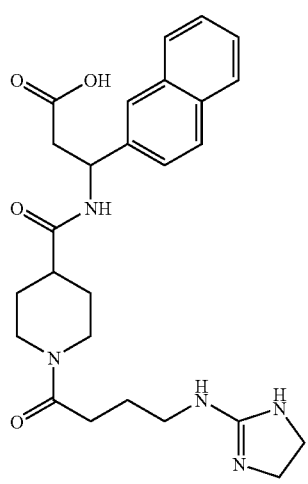
38 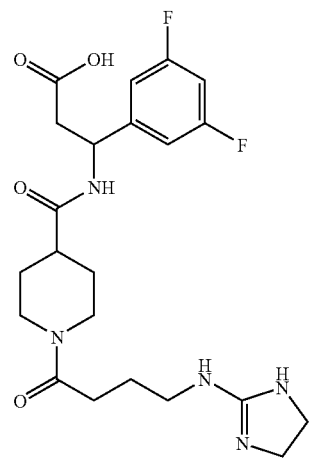
39 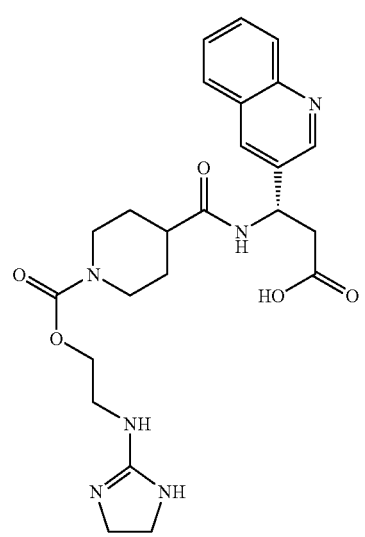
40 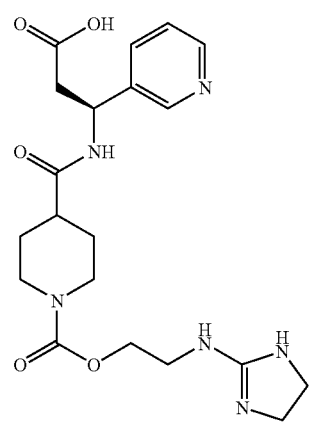

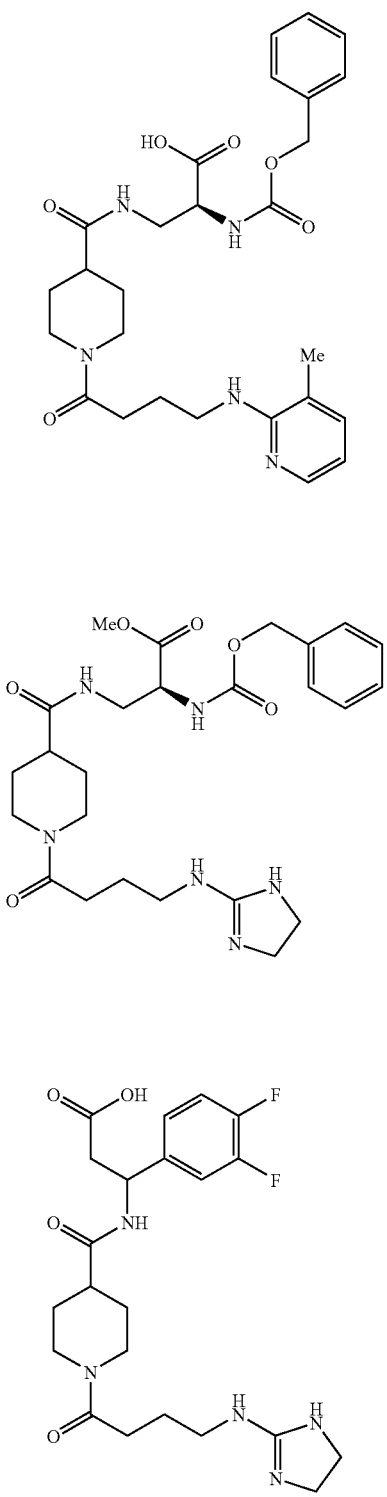
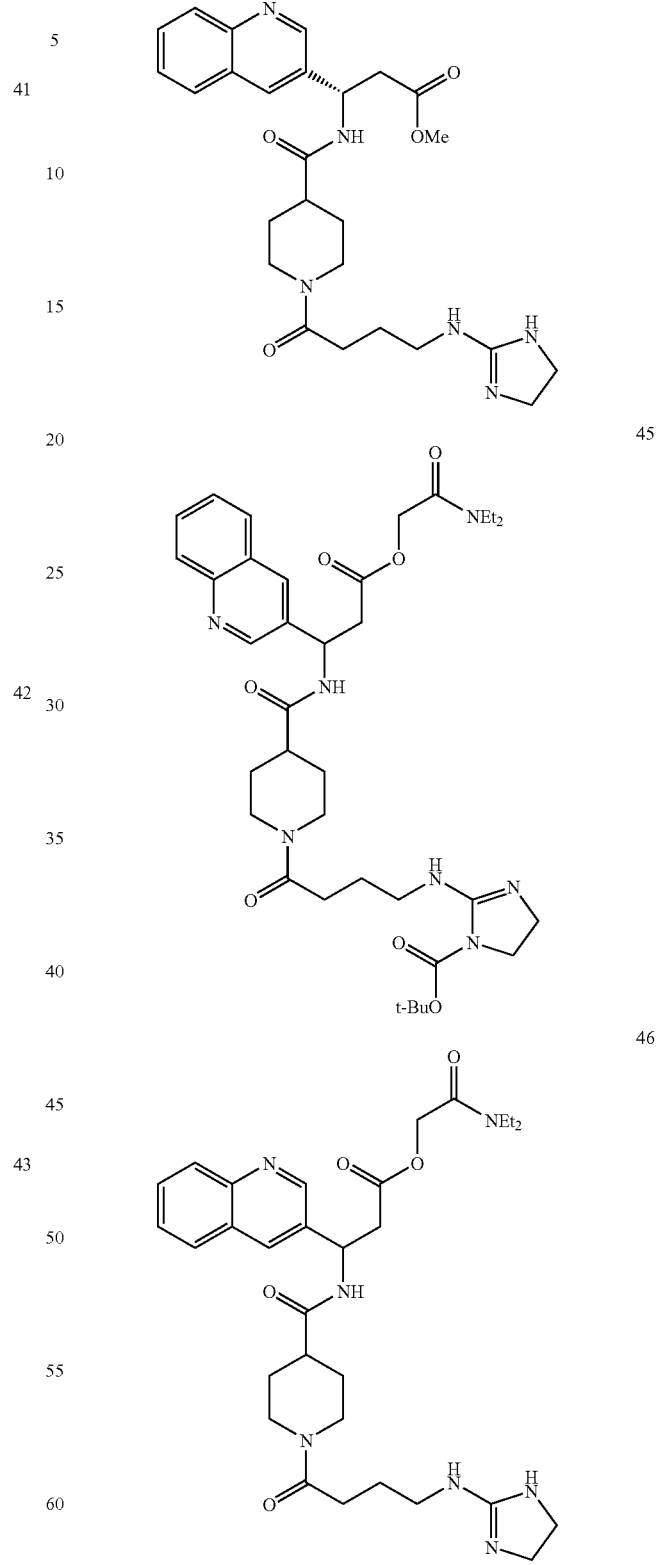

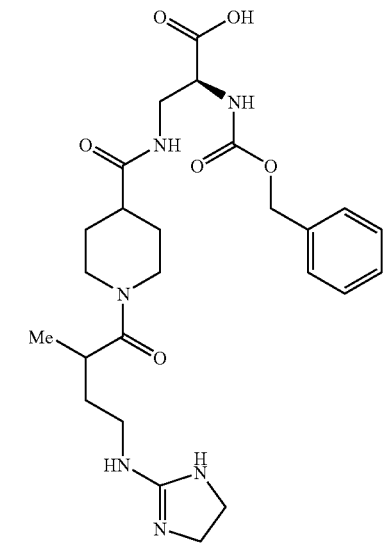
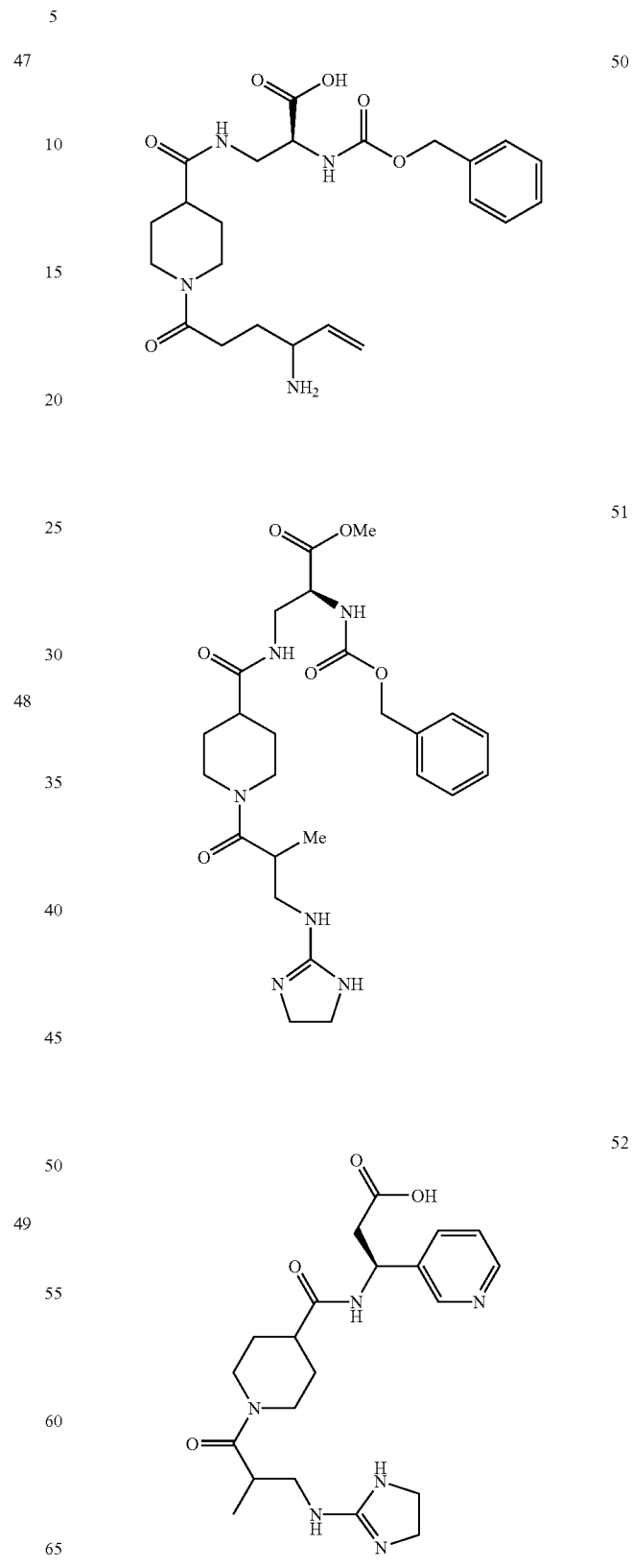

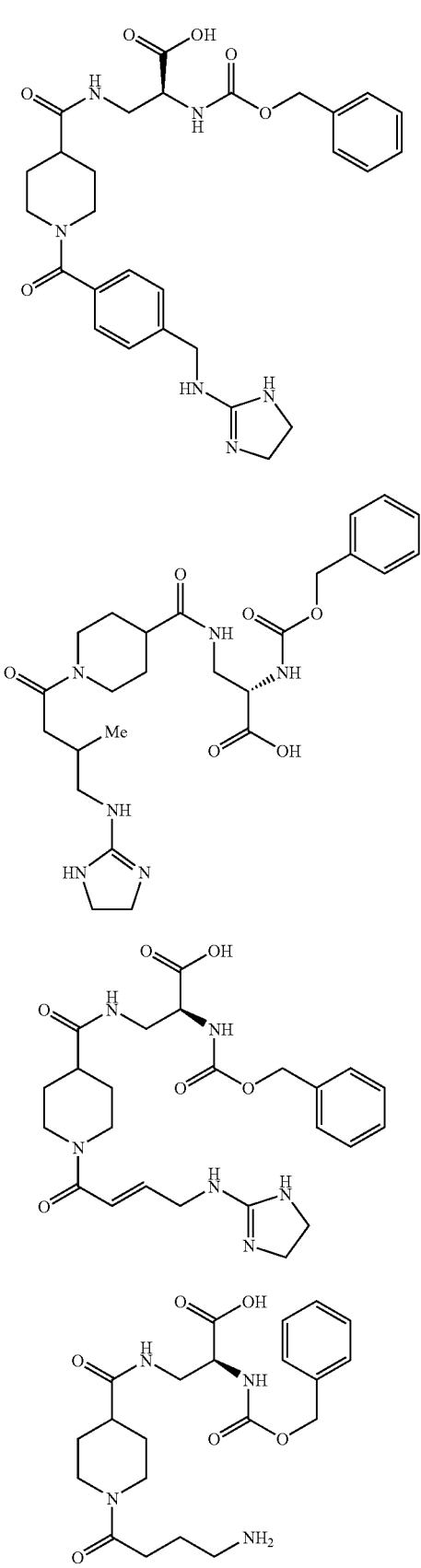
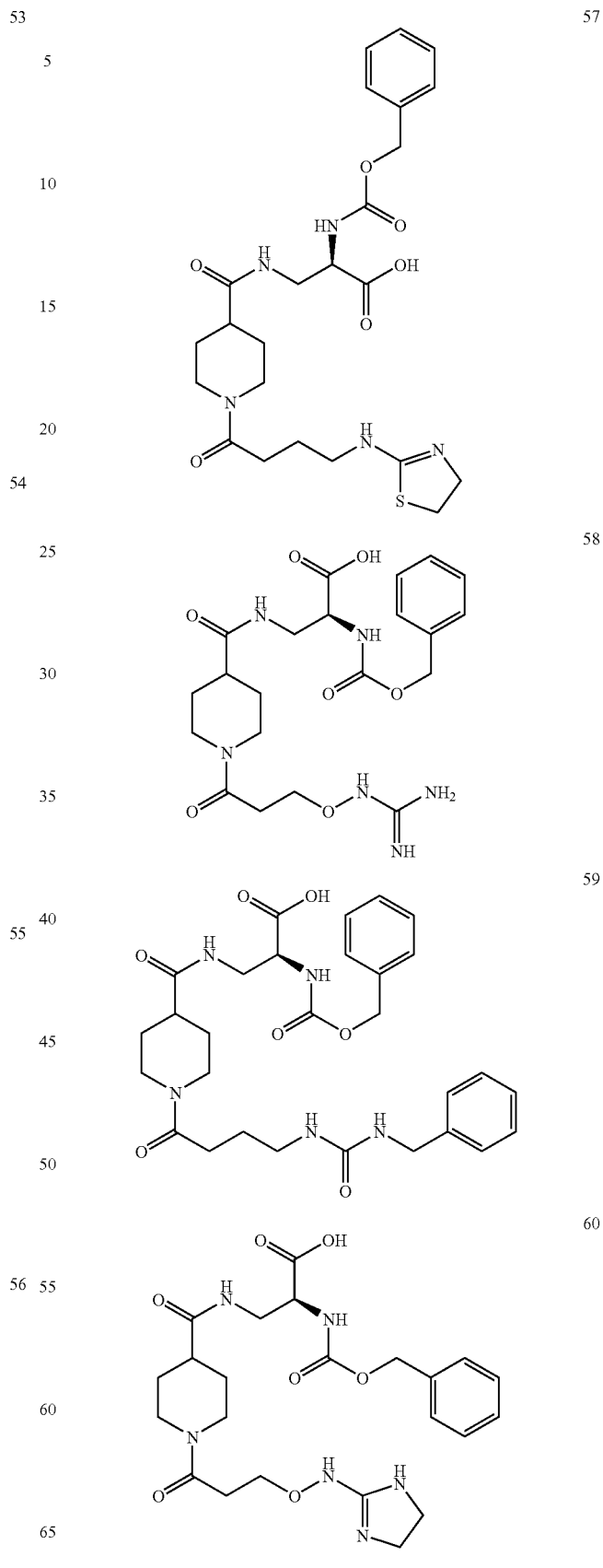

-continued

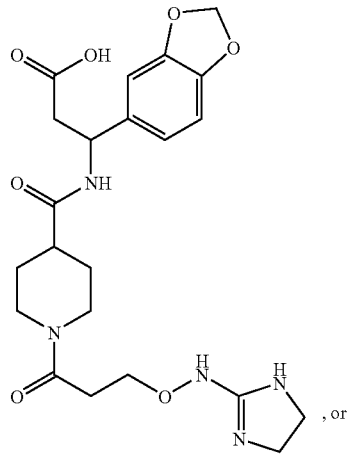

, or

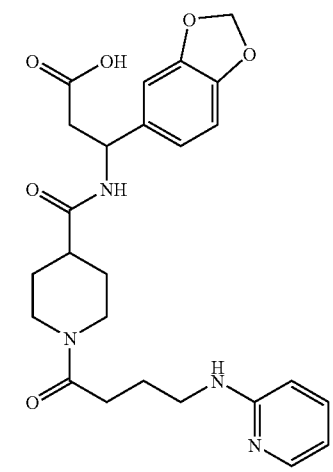

and pharmaceutically acceptable salts thereof.

Particularly preferred compounds of Formula (I) are selected from:

| Cpd | Name |
|---|---|
| 1 | β-[[[1-[4-[(4,5-dihydro-1H-imidazol-2-yl)amino]-1-oxobutyl]-4-piperidinyl]carbonyl]amino]-, (β$^3$S)- 3-quinolinepropanoic acid; |
| 2 | 3-[[[1-[4-[(4,5-dihydro-1H-imidazol-2-yl)amino]-1-oxobutyl]-4-piperidinyl]carbonyl]amino]-N-[(phenylmethoxy)carbonyl]-L-alanine; |
| 6 | β-[[[1-[1-oxo-4-(2-pyridinylamino)butyl]-4-piperidinyl]carbonyl]amino]-, (β$^3$S)- 3-quinolinepropanoic acid; |
| 11 | 3-[[[1-[[1-(4,5-dihydro-1H-imidazol-2-yl)-4-piperidinyl]carbonyl]-4-piperidinyl]carbonyl]amino]-N-[(phenylmethoxy)carbonyl]-L-alanine; |
| 14 | 3-[[[1-[[(1S,4R)-4-[(4,5-dihydro-1H-imidazol-2-yl)amino]-2-cyclopenten-1-yl]carbonyl]-4-piperidinyl]carbonyl]amino]-N-[(phenylmethoxy)carbonyl]-L-alanine; |
| 16 | 3-[[[1-[3-[(4,5-dihydro-1H-imidazol-2-yl)amino]-2-methyl-1-oxopropyl]-4-piperidinyl]carbonyl]amino]-N-[(phenylmethoxy)carbonyl]-L-alanine; |
| 17 | 3-[[[1-[[(1R,4S)-4-[(4,5-dihydro-1H-imidazol-2-yl)amino]-2-cyclopenten-1-yl]carbonyl]-4-piperidinyl]carbonyl]amino]-N-[(phenylmethoxy)carbonyl]-L-alanine; |
| 28 | 4-[[[(2S)-2-carboxy-2-[[(phenylmethoxy)carbonyl]amino]ethyl]amino]carbonyl]-, 2-[(4,5-dihydro-1H-imidazol-2-yl)amino]ethyl ester 1-piperidinecarboxylic acid; |
| 39 | β-[[[1-[[2-[(4,5-dihydro-1H-imidazol-2-yl)amino]ethoxy]carbonyl]-4-piperidinyl]carbonyl]amino]-, (β$^3$S)-3-quinolinepropanoic acid; |
| 47 | 3-[[[1-[4-[(4,5-dihydro-1H-imidazol-2-yl)amino]-2-methyl-1-oxobutyl]-4-piperidinyl]carbonyl]amino]-N-[(phenylmethoxy)carbonyl]-L-alanine; |
| 50 | 3-[[[1-(4-amino-1-oxo-5-hexenyl)-4-piperidinyl]carbonyl]amino]-N-[(phenylmethoxy)carbonyl]-L-alanine; |
| 53 | 3-[[[1-[4-[[(4,5-dihydro-1H-imidazol-2-yl)amino]methyl]benzoyl]-4-piperidinyl]carbonyl]amino]-N-[(phenylmethoxy)carbonyl]-L-alanine; |
| 61 | β-[[[1-[3-[[(4,5-dihydro-1H-imidazol-2-yl)amino]oxy]-1-oxopropyl]-4-piperidinyl]carbonyl]amino]- 1,3-benzodioxole-5-propanoic acid; or, |
| 62 | β-[[[1-[1-oxo-4-(2-pyridinylamino)butyl]-4-piperidinyl]carbonyl]amino]- 1,3-benzodioxole-5-propanoic acid; | and pharmaceutically acceptable salts thereof.

Representative Chemical Abstracts Service (CAS) Index-like names for the compounds of the present invention were derived using the ACD/LABS SOFTWARE™ Index Name Pro Version 4.0 nomenclature software program provided by Advanced Chemistry Development, Inc., Toronto, Ontario, Canada.

The compounds of the present invention may also be present in the form of pharmaceutically acceptable salts. For use in medicine, the salts of the compounds of this invention refer to non-toxic "pharmaceutically acceptable salts." Other salts may, however, be useful in the preparation of compounds according to this invention or of their pharmaceutically acceptable salts. The pharmaceutically acceptable salts generally take a form in which a basic nitrogen or nitrogens on the compound of the Formula (I) are protonated with an inorganic or organic acid. Representative inorganic or organic acids include, but are not limited to, hydrochloric, hydrobromic, hydriodic, perchloric, sulfuric, nitric, phosphoric, acetic, propionic, glycolic, lactic, succinic, maleic, fumaric, malic, tartaric, citric, benzoic, mandelic, methanesulfonic, hydroxyethanesulfonic, benezenesulfonic, oxalic, pamoic, 2-naphthalenesulfonic, p-toluenesulfonic, cyclohexanesulfamic, salicylic, saccharinic or trifluoroacetic acid. Similarly, pharmaceutically acceptable salts also include compounds wherein a carboxylic acid group of the compound of the Formula (I) combines with a organic or inorganic base. Representative inorganic or organic bases include, but are not limited to lithium, sodium, potassium, magnesium, calcium, aluminum, zinc, benzathine, chloroprocaine, choline, diethanolamine, ethylenediamine, meglumine (N-methyl glucamine), tromethamine (2-amino-2-(hydroxymethyl)-1,3-propanediol) or procaine (4-amino-[2-(diethylamino)ethyl ester] benzoic acid).

As used herein, unless otherwise noted alkyl and alkoxy when used alone include straight and branched chains having 1 to 8 carbon atoms, or any number within this range. Similarly, alkenyl and alkynyl groups include straight and branched chain alkenes and alkynes having 2 to 8 carbon atoms, or any number within this range. The term alkylene, alkenylene and alkynylene refers to alkyl, alkenyl and alkynyl chains, respectively, that are further substituted and act as linking groups.

Alkoxy radicals are oxygen ethers formed from the previously described straight or branched chain alkyl groups. Cycloalkyl groups contain 3 to 8 ring carbons; preferably, 5 to 8 ring carbons; and, more preferably, 5 to 7 ring carbons.

The term "heterocyclyl" as used herein refers to an optionally substituted, stable, saturated 3 to 10 (preferably 4 to 8) membered monocyclic or bicyclic ring system which consists of carbon atoms and from one to three heteroatoms selected from N, O or S. The term "heterocyclenyl" as used herein refers to an optionally substituted, stable, unsaturated 3 to 10 (preferably 4 to 8) membered monocyclic or bicyclic ring system which consists of carbon atoms and from one to three heteroatoms selected from N, O or S. The heterocyclyl or heterocyclenyl group may be attached at any heteroatom or carbon atom which results in the creation of a stable structure and, accordingly, may be further attached to, for example, alkyl or alkoxy chains. The term hetercyclylene and heterocyclenylene refers to hetercyclyl and heterocyclenyl groups, respectively, that are further substituted and act as linking groups; wherein, one or both rings may be optionally substituted with one to five substituents attached at any heteroatom or carbon atom which results in the creation of a stable structure.

The term "aryl", as used herein, refers to optionally substituted aromatic groups such as phenyl and naphthyl. The term arylene refers to aryl groups that are further substituted and act as linking groups; wherein, one or both rings may be optionally substituted with one to five substituents attached at any carbon atom which results in the creation of a stable structure.

The term "heteroaryl" as used herein represents a stable five or six membered monocyclic aromatic ring system or a nine or ten membered benzo-fused heteroaromatic ring system which consists of carbon atoms and from one to three heteroatoms selected from N, O or S. The heteroaryl group may be attached or optionally substituted at any heteroatom or carbon atom which results in the creation of a stable structure.

The term "arylalkyl" means an alkyl group substituted with an aryl group (e.g., benzyl, phenethyl). Similarly, the term "arylalkoxy" indicates an alkoxy group substituted with an aryl group (e.g., benzyloxy).

The term "acyl" as used herein means an organic radical having 2 to 6 carbon atoms (branched or straight chain) derived from an organinc acid by removal of the hydroxy group.

Whenever the term "alkyl" or "aryl" or either of their prefix roots appear in a name of a substituent (e.g., aralkyl, alkylamino) it shall be interpreted as including those limitations given above for "alkyl" and "aryl." When present, designated numbers of carbon atoms (e.g., $C_1$-$C_8$) shall refer independently to the number of carbon atoms in a moiety or to the alkyl portion of a larger substituent in which alkyl appears as its prefix root.

Any of the foregoing cycloalkyl, heterocyclyl, heterocyclenyl, aryl and heteroaryl substituent groups and their corresponding heterocyclylene, heterocyclenylene, arylene and heteroarylene linking groups, as a monocyclic or bicyclic ring system may be further bridged at any heteroatom or carbon atom which results in the creation of a stable ring structure; wherein the monocyclic bridged ring system consists of 6 to 8 members and the bicyclic bridged ring system consists of 10 to 12 members.

It is intended that the definition of any substituent or variable at a particular location in a molecule be independent of its definitions elsewhere in that molecule. It is understood that substituents and substitution patterns on the compounds of this invention can be selected by one of ordinary skill in the art to provide compounds that are chemically stable and that can be readily synthesized by techniques know in the art as well as those methods set forth herein.

Under standard nomenclature used throughout this disclosure, the terminal portion of the designated side chain is described first, followed by the adjacent functionality toward the point of attachment. Thus, for example, a "phenyl$C_1$-$C_6$ alkylamido$C_1$-$C_6$alkyl" substituent refers to a group of the formula:

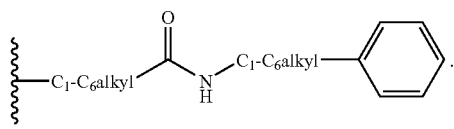

The present invention includes within its scope prodrugs of the compounds of this invention. In general, such prodrugs will be functional derivatives of the compounds which are readily convertible in vivo into the required compound. Examples of prodrugs include but are not limited to various esters, hydroxyamidines and hydroxyguanidines of compounds of the present invention. Thus, in the methods of treatment of the present invention, the term "administering" shall encompass the treatment of the various disorders described with the compound specifically disclosed or with a compound which may not be specifically disclosed, but which converts to the specified compound in vivo after administration to the patient. Conventional procedures for the selection and preparation of suitable prodrug derivatives are described, for example, in "Design of Prodrugs", ed. H. Bundgaard, Elsevier, 1985.

Where the compounds according to this invention have at least one chiral center, they may accordingly exist as enantiomers. Where the compounds possess two or more chiral centers, they may additionally exist as diastereomers. It is to be understood that all such isomers and mixtures thereof are encompassed within the scope of the present invention. Furthermore, some of the crystalline forms for the compounds may exist as polymorphs and as such are intended to be included in the present invention. In addition, some of the compounds may form solvates with water (i.e., hydrates) or common organic solvents, and such solvates are also intended to be encompassed within the scope of this invention.

The term "subject" as used herein, refers to an animal, preferably a mammal, most preferably a human, who has been the object of treatment, observation or experiment.

The term "therapeutically effective amount" as used herein, means that amount of active compound or pharmaceutical agent that elicits the biological or medicinal response in a tissue system, animal or human, that is being sought by a researcher, veterinarian, medical doctor, or other clinician, which includes alleviation of the symptoms of the disease or disorder being treated.

The term "bone resorption," as used herein, refers to the process by which osteoclasts degrade bone.

The present invention provides isonipecotamide compounds that are useful as αvβ3, αvβ5 and GPIIb/IIIa integrin antagonists. Compounds of Formula (I) that are particularly preferred as αvβ3 integrin antagonists are selected from Compound 1, 2, 3, 5, 6, 12, 14, 16, 18, 21, 24, 25, 28, 29, 31, 33, 34, 39, 40, 44, 47, 49, 54, 55, 58 or 60. Compounds of Formula (I) that are particularly preferred as GPIIb/IIIa integrin antagonists are selected from Compound 1, 2, 5, 11, 12, 14, 16, 17, 18, 19, 39, 47, 49, 50, 53, 54, 55 or 56. Compounds of Formula (I) that are particularly preferred as αvβ5 integrin antagonists are selected from Compound 1, 2, 16, 45, 58 or 60. Compounds of Formula (I) that are particularly preferred as dual αvβ3/GPIIb/IIIa integrin antagonists are selected from Compound 2, 5, 12, 14, 16, 18, 39, 47, 49, 54 or 55. Compounds of Formula (I) that are particularly preferred as dual αvβ3/αvβ5 integrin antagonists are selected from Compound 1, 2, 16, 58 or 60.

Compounds of Formula (I) that are more particularly preferred as αvβ3 integrin antagonists are selected from Compound 1, 2, 6, 28, 39 or 47. Compounds of Formula (I) that are more particularly preferred as GPIIb/IIIa integrin antagonists are selected from Compound 2, 11, 14, 17, 50 or 53. Compounds of Formula (I) that are more particularly preferred as αvβ5 integrin antagonists are selected from Compound 1, 2 or 16. Compounds of Formula (I) that are more particularly preferred as dual αvβ3/GPIIb/IIIa integrin antagonists are Compound 2. Compounds of Formula (I) that are more particularly preferred as dual αvβ3/αvβ5 integrin antagonists are selected from Compound 1 or 2.

The compounds of Formula (I) inhibit the binding of adhesive proteins such as fibrinogen, vitronectin, and osteopontin to the integrin class of receptors. As demonstrated by the results of the biological studies described hereinafter, the compounds block vitronectin binding to isolated αvβ3 ($IC_{50}$'s of ca. 1-300 nM), and inhibit fibrinogen binding to isolated GPIIb/IIIa as well. Because the compounds of this invention inhibit integrin-mediated cell-cell or cell-matrix adhesion, they may be useful against restenosis, thrombosis, inflammation, atherosclerosis, arthritis, angiogenesis, osteoporosis, bone resorption, tumor cell metastasis, tumor growth, macular degeneration, diabetic retinopathy, diseases of lung/airway resistance, etc. (D. Cox, *Drug News & Perspectives* 1995, 8, 197).

The compounds of Formula (I) are also useful as antithrombotics in combination with fibrinolytic therapy (e.g., t-PA or streptokinase). Additionally, the compounds of Formula (I) are useful in combination with one or more agents useful in the prevention or treatment of osteoporosis and arthritis. For example, the compounds of the instant invention may be effectively administered in combination with other agents used in the treatment of osteoporosis such as bisphosphonate bone resorption inhibitors; preferably, the bisphosphonate bone resorption inhibitor is alendronate, sold as FOSAMAX®. Preferred combinations are simultaneous or alternating treatments of an integrin antagonist of the present invention and alendronate.

In accordance with the methods of the present invention, the individual components of the combination can be administered separately at different times during the course of therapy or concurrently in divided or single combination forms. The instant invention is therefore to be understood as embracing all such regimes of simultaneous or alternating treatment and the term "administering" is to be interpreted accordingly.

As used herein, the term "composition" is intended to encompass a product comprising the specified ingredients in the specified amounts, as well as any product which results, directly or indirectly, from combinations of the specified ingredients in the specified amounts.

The utility of the compounds to treat integrin-mediated disorders can be determined according to the procedures herein. The present invention therefore provides a method of treating integrin-mediated disorders in a subject in need thereof which comprises administering any of the compounds as defined herein in a quantity effective to treat thrombotic disorders, osteoporosis, cancer, and diabetic complications. The compound may be administered to a patient by any conventional route of administration, including, but not limited to, intravenous, oral, subcutaneous, intramuscular, intradermal and parenteral.

The present invention also provides pharmaceutical compositions comprising one or more compounds of this invention in association with a pharmaceutically acceptable carrier.

To prepare the pharmaceutical compositions of this invention, one or more compounds of Formula (I) or salt thereof of the invention as the active ingredient, is intimately admixed with a pharmaceutical carrier according to conventional pharmaceutical compounding techniques, which carrier may take a wide variety of forms depending of the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be sugar coated or enteric coated by standard techniques. For parenterals, the carrier will usually comprise sterile water, through other ingredients, for example, for purposes such as aiding solubility or for preservation, may be included. Injectable suspensions may also be prepared, in which case appropriate liquid carriers, suspending agents and the like may be employed. The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, of from about 0.01 mg/kg to 100 mg/kg (preferably, from about 0.1 mg/kg to about 30 mg/kg) and may be given at a dosage of from about 0.01 mg/kg/day to about 300 mg/kg/day (preferably, from about 1 mg/kg/day to about 50 mg/kg/day). The dosages, however, may be varied depending upon the requirement of the patients, the severity of the condition being treated and the compound being employed. The use of either daily administration or post-periodic dosing may be employed.

Preferably these compositions are in unit dosage forms from such as tablets, pills, capsules, powders, granules, sterile parenteral solutions or suspensions, metered aerosol or liquid sprays, drops, ampoules, autoinjector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a pharmaceutically acceptable salt thereof. When referring to these preformulation compositions as homogeneous, it is meant that the active ingredient is dispersed evenly throughout the composition so that the composition may be readily subdivided into equally effective dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, cetyl alcohol and cellulose acetate.

The liquid forms in which the novel compositions of the present invention may be incorporated for administration orally or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin.

Where the processes for the preparation of the compounds according to the invention give rise to mixture of stereoisomers, these isomers may be separated by conventional techniques such as preparative chromatography. The compounds may be prepared in racemic form, or individual enantiomers may be prepared either by enantiospecific synthesis or by resolution. The compounds may, for example, be resolved into their components enantiomers by standard techniques, such as the formation of diastereomeric pairs by salt formation with an optically active acid, such as (−)-di-p-toluoyl-d-tartaric acid and/or (+)-di-p-toluoyl-l-tartaric acid followed by fractional crystallization and regeneration of the free base. The compounds may also be resolved by formation of diastereomeric esters or amides, followed by chromatographic separation and removal of the chiral auxiliary. Alternatively, the compounds may be resolved using a chiral HPLC column.

During any of the processes for preparation of the compounds of the present invention, it may be necessary and/or desirable to protect sensitive or reactive groups on any of the molecules concerned. This may be achieved by means of conventional protecting groups, such as those described in *Protective Groups in Organic Chemistry*, ed. J. F. W. McOmie, Plenum Press, 1973; and T. W. Greene & P. G. M. Wuts, *Protective Groups in Organic Synthesis; Third Edition*, John Wiley & Sons, 1999. The protecting groups may be removed at a convenient subsequent stage using methods known from the art.

The method of treating integrin-mediated disorders described in the present invention may also be carried out using a pharmaceutical composition comprising any of the compounds as defined herein and a pharmaceutically acceptable carrier. The pharmaceutical composition may contain between about 0.01 mg and 100 mg, preferably about 5 to 50 mg, of the compound, and may be constituted into any form suitable for the mode of administration selected. Carriers include necessary and inert pharmaceutical excipients, including, but not limited to, binders, suspending agents, lubricants, flavorings, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions.

Advantageously, compounds of the present invention may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The liquid forms in suitably flavored suspending or dispersing agents such as the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

The compound of the present invention can also be administered in the form of liposome delivery systems, such as small unilamellar vesicles, large unilamellar vesicles, and multilamellar vesicles. Liposomes can be formed from a variety of phospholipids, such as cholesterol, stearylamine or phophatidylcholines.

Compounds of the present invention may also be delivered by the use of monoclonal antibodies as individual carriers to which the compound molecules are coupled. The compounds of the present invention may also be coupled with soluble polymers as targeted drug carriers. Such polymers can include polyvinylpyrrolidone, pyran copolymer, polyhydroxypropylmethacrylamidephenol, polyhydroxy-ethylaspartamidephenol, or polyethyl eneoxidepolylysine substituted with palmitoyl residue. Furthermore, the compounds of the present invention may be coupled to a class of biodegradable polymers useful in achieving controlled release of a drug, for example, polylactic acid, polyepsilon caprolactone, polyhydroxy butyeric acid, polyorthoesters, polyacetals, polydihydropyrans, polycyanoacrylates and cross-linked or amphipathic block copolymers of hydrogels.

Compounds of this invention may be administered in any of the foregoing compositions and according to dosage regimens established in the art whenever treatment of thrombotic disorders is required.

The daily dosage of the products may be varied over a wide range from about 0.01 mg to about 21,000 mg per adult human per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. A therapeutically effective amount of the drug is ordinarily supplied at a dosage level of from about 0.01 mg/kg to about 300 mg/kg of body weight per day. Preferably, the range is from about 0.01 mg/kg to about 100 mg/kg of body weight per day; and more preferably, the range is from about 0.01 mg/kg to about 50 mg/kg of body weight per day. The compounds may be administered on a regimen of 1 to 4 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

Abbreviations used in the instant specification, particularly the Schemes and Examples, are as follows:

| | |
|---|---|
| Aq. = | aqueous |
| Bn or Bzl = | benzyl |
| Boc = | tert-butoxycarbonyl |
| Boc$_2$O | di-tert-butyl dicarbonate |
| BSA = | bovine serum albumin |
| n-Bu = | n-butyl |
| Cbz = | benzyloxycarbonyl |
| CP or Cpd = | Compound |
| DCM = | dichloromethane |
| DIC = | diisopropylcarbodiimide |
| DIPEA = | diisopropylethylamine |
| DMAP = | 4-dimethylaminopyridine |
| DMF = | N,N-dimethylformamide |
| DMSO = | dimethylsulfoxide |
| EDC = | ethyl dimethylaminopropyl-carbodiimide |
| EDTA = | ethylenediaminetetraacetic acid |
| ES = | electrospray |
| Et = | ethyl |
| Et$_2$O = | diethyl ether |
| EtOH = | ethanol |
| $^1$H NMR = | proton nuclear magnetic resonance spectrum |
| HBTU = | 2-(1H-benzotriazole-1-yl)-1,1,3,3-tetramethyluronium hexafluorophosphate |
| HEPES = | 4-(2-hydroxyethyl)-1-piperazine-ethanesulfonic acid |
| HOBT = | hydroxybenzotriazole |
| HBTU = | 2-(1H-benzotriazole-1-yl)-1,1,3,3-tetramethyl-uronium hexafluorophosphate |
| IPA = | 2-propanol |
| Me = | methyl |
| MeOH = | methanol |
| MH$^+$ = | observed molecular ion |
| MPK = | milligrams per kilogram |
| MS = | mass spectrum |
| NMM = | N-methylmorpholine |
| NT = | not tested |
| Ph = | phenyl |
| PPT = | precipitate |
| Pyr. = | pyridine |
| RP-HPLC = | preparative reversed-phase high pressure liquid chromatography |
| RT = | room temperature |
| Sch = | Scheme |
| TEA = | triethylamine |
| THF = | tetrahydrofuran |
| TFA = | trifluoroacetic acid |
| TMS = | trimethylsilane |
| Z = | benzyloxycarbonyl |

General Synthetic Methods

Although the following Schemes depict synthetic routes to specific compounds of Formula (I), they are intended to also represent general synthetic routes to other compounds of the present invention to those skilled in the art of synthetic organic chemistry. By way of example, the synthetic route shown in Scheme AA used to prepare Compound 1 is also illustrative of a general method for the preparation of other instant compounds whereby other starting materials and appropriate reagents and solvents are used.

Scheme AA

Compounds of the invention wherein A is 4,5-dihydro-2-imidazolylamino and its homologs may be prepared as shown below. β-Aminoacid derivative AA5 was prepared as detailed in PCT International Application WO 97/41102 and as published (J. Rico, J. Org. Chem. 1993, 58, 7948). Such β-aminoacid derivatives can also be prepared by the methods described in WO 97/08145 and in U.S. Pat. No. 6,100,423. The reagent AA3 was purchased from Maybridge Chemical Company.

For the preparation of compounds exemplified by final target Compound 1, secondary amine AA1 was acylated with EDC-activated 4-N-Boc-aminobutyric acid, and the Boc group subsequently removed with trifluoroacetic acid to give primary amine AA2 as the TFA salt. This salt was acylated with reagent AA3, the 2-aminoimidazoline product was protected with di-tert-butyl dicarbonate, and the methyl ester was saponified with lithium hydroxide to afford AA4. Intermediate AA4 was acylated with HBTU-activated amino ester AA5, and this product was then de-protected with aqueous hydrochloric acid to give the target Compound 1. Similarly, the Boc group of coupling product from AA4 and AA5 can be removed with a mixture of trifluoroacetic acid in dichloromethane (1:1) and the ester moiety subsequently saponified with aqueous LiOH in tetrahydrofuran to afford the lithium salt of Compound 1. If the ester derivative is desired, then the saponification step is eliminated. For the preparation of other compounds of the invention, such as those exemplified by the α-diaminoalkanoic acid derivative Compound 11, the secondary amine AA1 was reacted with the appropriate acid and carried forward as shown for the steps from AA2 to AA4 in Scheme AA, replacing AA5 with AB2 to produce the target Compound 11.

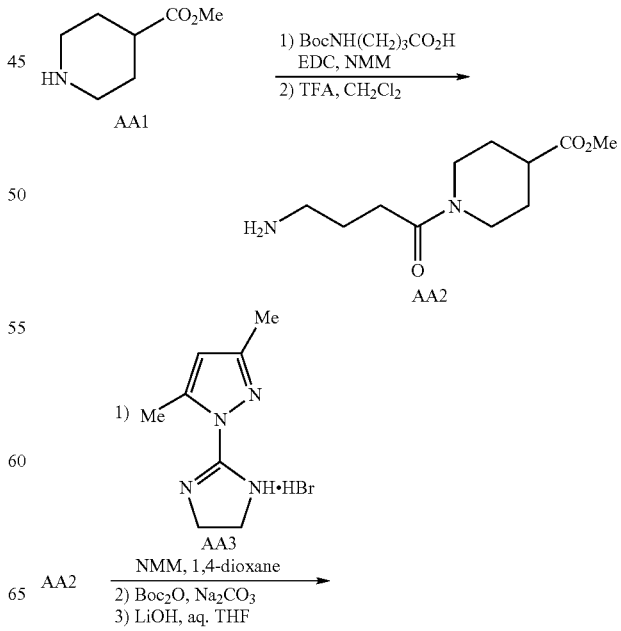

SCHEME AB

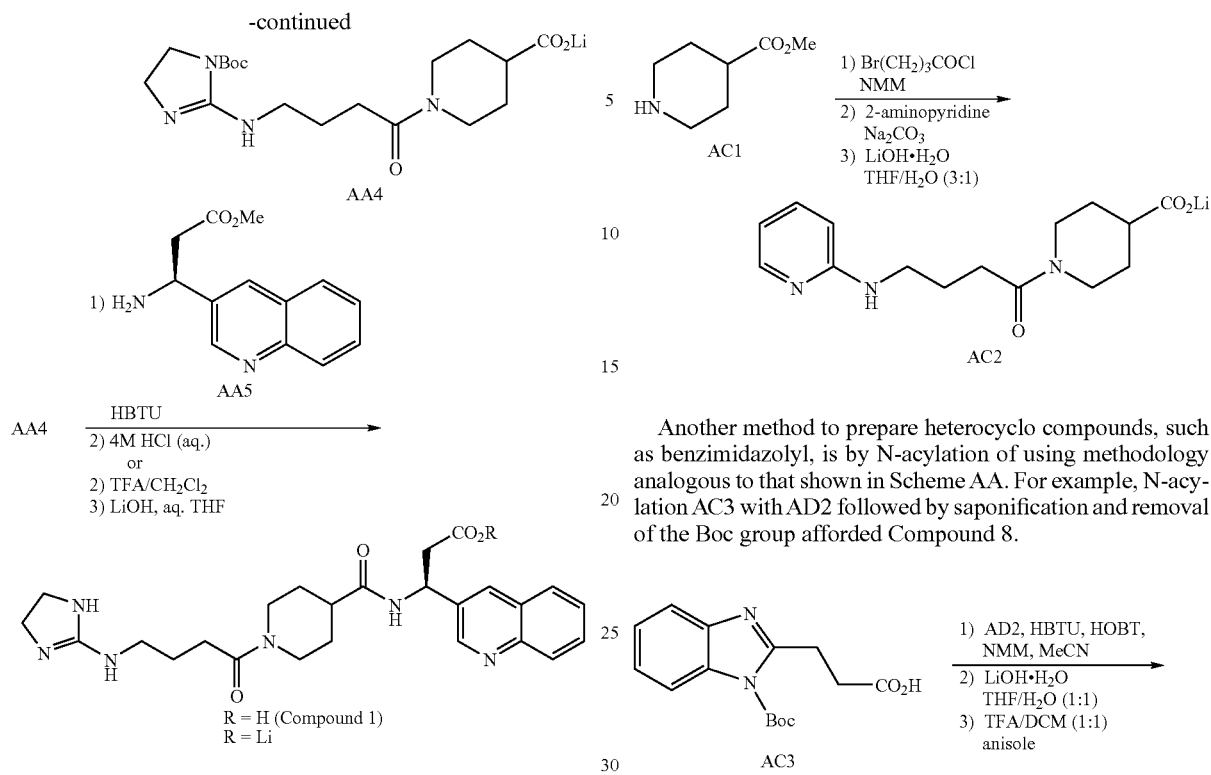

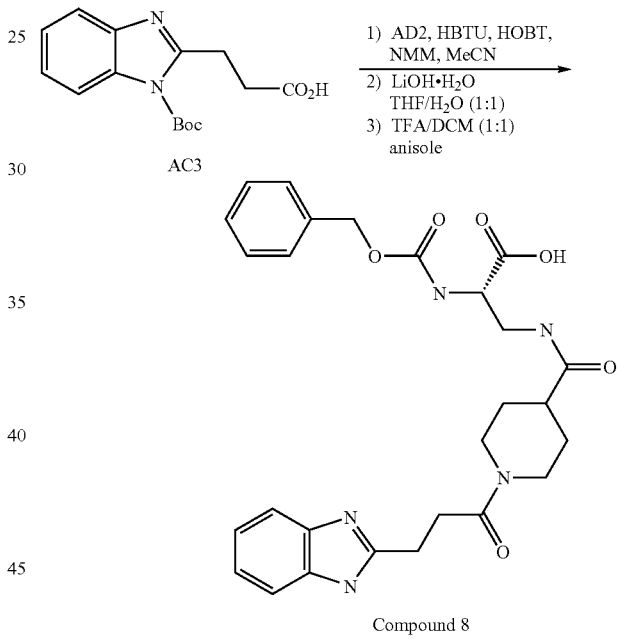

Another method to prepare heterocyclo compounds, such as benzimidazolyl, is by N-acylation of using methodology analogous to that shown in Scheme AA. For example, N-acylation AC3 with AD2 followed by saponification and removal of the Boc group afforded Compound 8.

Preparation of α-diaminoalkanoic acid derivatives of Formula (I), such as Compound 2, can be prepared from ester intermediates such as AB2 (methyl N-60-(benzyloxycarbonyl)-L-2,3-diaminopropionate). In this example, Cbz-protected acid AB1 (purchased from BaChem) was dissolved in methanol and treated with 4N HCl in 1,4-dioxane in the presence of 1,2-dimethoxypropane to afford the intermediate amino ester AB2. Using the method described in Scheme AA, AB2 replaced AA5 to produce Compound 2.

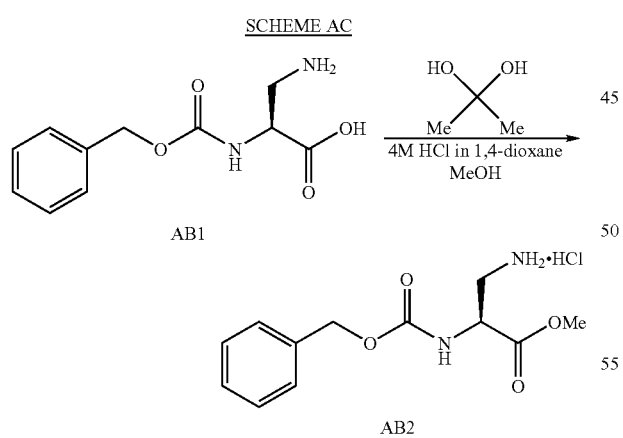

Compounds of Formula (I) wherein A is heterocyclo or heterocyclo-2-amino can be prepared the reaction of 2-aminoheterocycles with the appropriate alkyl halide. For example, Compound AC1 was acylated with 4-bromobutyryl chloride and the resulting alkyl bromide product was reacted with 2-aminopyridine at reflux to provide AC2. Ester AC2 was saponified with lithium hydroxide and carried forward as shown for AA4 in Scheme AA to give Compound 7.

Certain other heterocyclo-2-amino compounds may be prepared by reacting a 2-fluoroheterocycle with the appropriate aminoalkanoate (e.g., AA2) as reported by C. Senanayake in *Tetrahedron Lett.* 1999, 40, 6875. For compounds where A is tetrahydro-2-pyrimidinylamino or 2-pyrimidinylamino, 2-bromopyrimidine may be reacted with the appropriate aminoalkanoate (e.g., AA2) as reported by G. Hartman in WO 95/3271,0. For compounds where A is imidazo-4-pyridin-2-yl, an appropriate alkyl dicarboxylic acid (e.g., succinic acid) may be reacted with 2,3-diaminopyridine as reported by R. Keenan in *Bioorg. Med. Chem. Lett.* 1998, 8, 3171.

Scheme AD

Scheme AD provides an alternate method of synthesis for the α-diaminoalkanoic acid derivatives of Formula (I), such as Compound 2, by changing the order of the coupling steps depicted in Scheme AA. For example, isonipecotamide intermediate AD2, used to synthesize Compound 2, was prepared by the HBTU-mediated coupling of AD1 (purchased from Advanced Chemtech) and AB2.

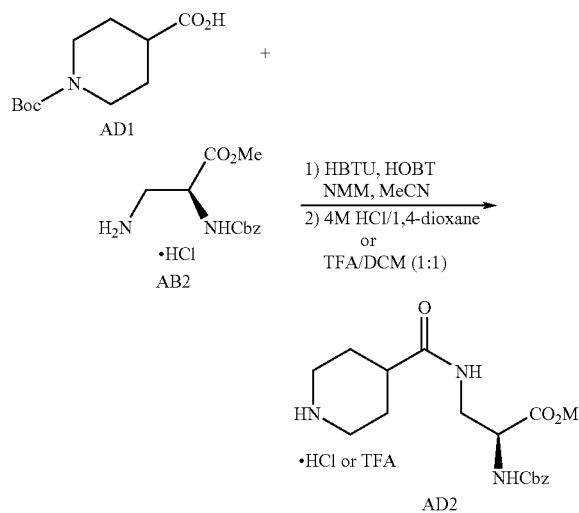

The acid AD3 was prepared (as described by J. V. Greenhill, *Chem. Soc., Perkin Trans.* 2 1985, (8), 1255-1264) and was reacted with di-tert-butyl dicarbonate in the presence of NaOH. The intermediate sodium salt was coupled with AD2 using HBTU to afford AD4. Deprotection of AD4 with 4 M HCl (aq.) yielded Compound 2.

SCHEME AE

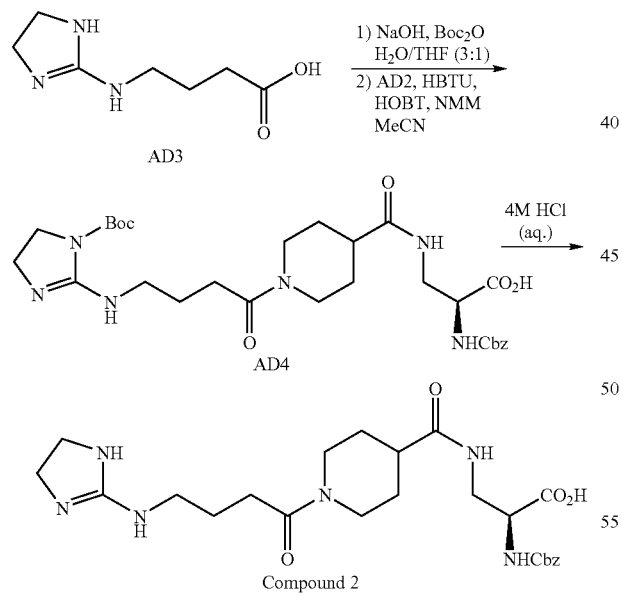

Compounds of Formula (I) wherein A is attached by an aminooxy group can be prepared by the methods represented below. Boc-protected aminooxy intermediates AE5 and AE8, used to prepare Compounds 58 and 61, respectively, were synthesized according to the methods described by C. Gilon et al. in *Tetrahedron* 1967, 23, 441-4447 and B. J. Ludwig in *J. Med. Chem.* 1970, 13, 60-63. Commercially available β-propriolactone (AE1) and N-hydroxysuccinimide (AE2) were reacted to afford the corresponding oxyamino ester, which was hydrolyzed in refluxing mixture of 6 M HCl (aq.) and glacial acetic acid. The resulting HCl salt was converted to the free base AE3 by treatment with NaOMe in 2-propanol. Guanylation of AE3 with commercially available AE4 followed by reaction with di-tert-butyl dicarbonate furnished protected oxyguanidine intermediate AE5, which was converted to Compound 58 by analogy to intermediate AA4 in Scheme AA.

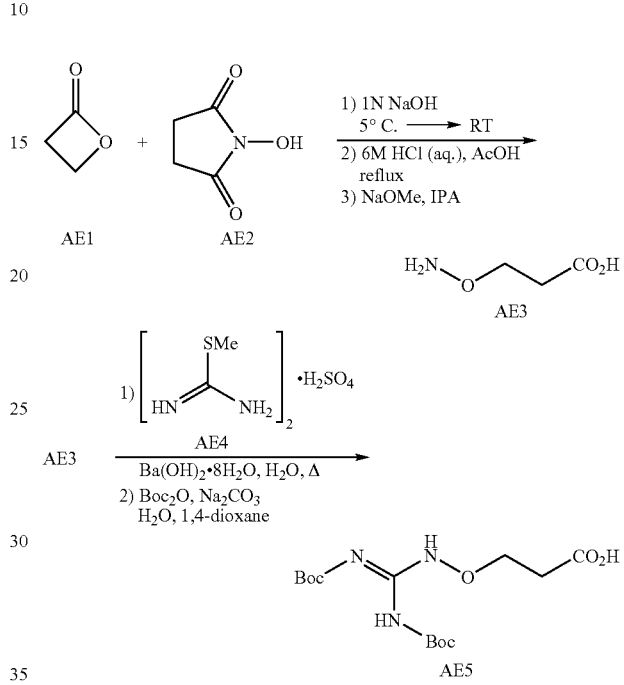

Similarly, Boc-protection of AE6 (purchased from Aldrich) followed by reaction with AE3 afforded protected (4,5-dihydroimidazol-2-yl)aminooxy intermediate AE8, which was converted to Compound 61 by analogy to intermediate AA4 in Scheme AA.

SCHEME AF

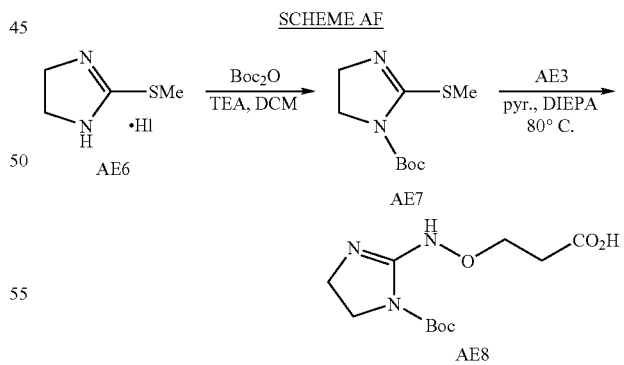

Compounds of Formula (I) wherein A is a urea moiety, such as Compound 59, may be prepared as depicted below. HBTU-mediated coupling of commercially available starting materials AF1 and AF2 and subsequent saponification of the intermediate ester furnished AF3, which was coupled with AB2 to give AF4. Deprotection of AF4 with TFA/DCM followed by reaction with phenyl isocyanate and hydrolysis of the resulting ester with 4 M HCl (aq.) yielded Compound 59.

SCHEME AG

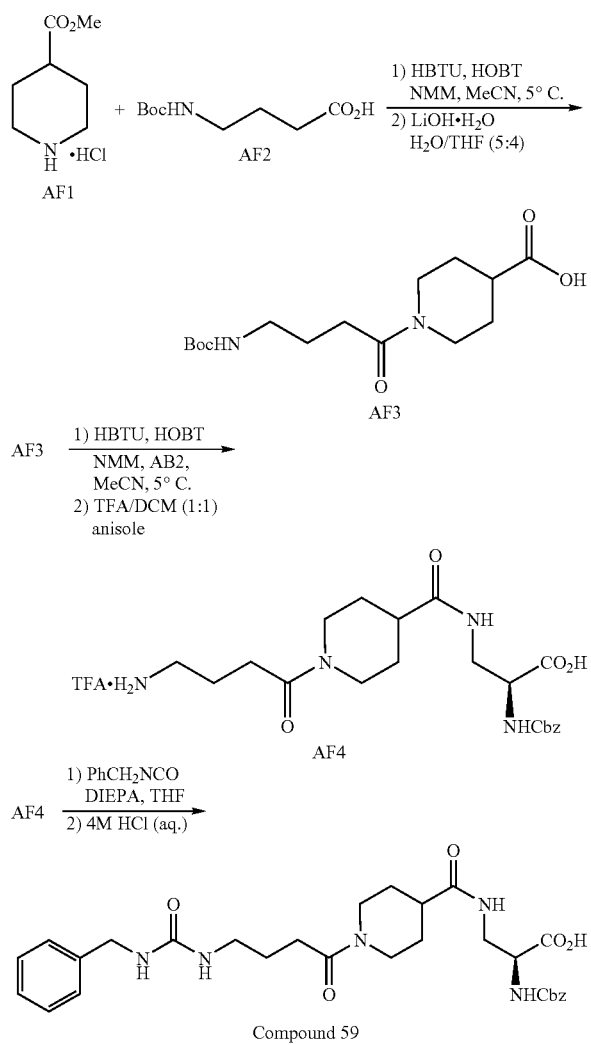

Compounds of the Formula (I) wherein A is heterocycloamino, may be prepared by reacting certain activated methylthio derivatives with the appropriate amine. For example, Compound 57 can be prepared by reacting AG1 (purchased from Aldrich) with amine AF4 followed by acid hydrolysis of the resulting ester.

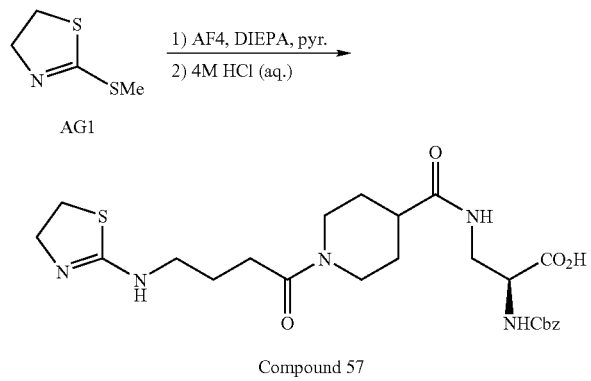

Similarly, activation of thiourea AG2, prepared as described in WO/0034255, with methyl iodide followed by reaction with AG3 as described in WO/9708145 could provide AG4, a member of the compounds of the Formula (I).

SCHEME AH

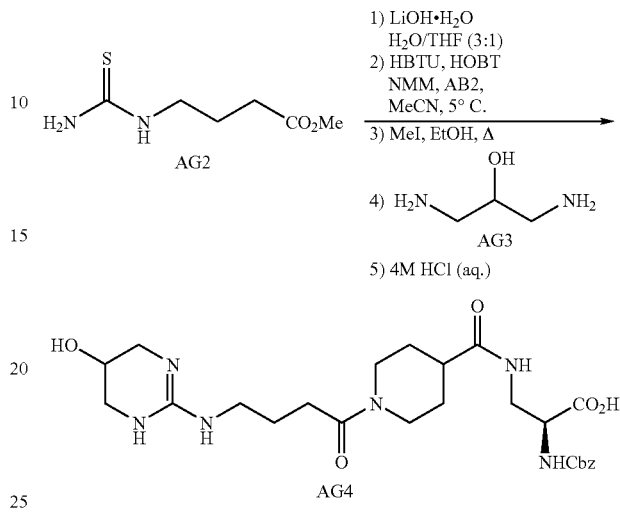

Compounds of the Formula (I) wherein L is OC(=O) or HNC(=O) can be prepared as outlined in below. A protected aminoalcohol, such as AH1, can be converted as shown to the corresponding p-nitrochloroformate. Reaction of the p-nitrochloroformate intermediate with AF1 followed by removal of the Boc group furnished an intermediate amine, which was subsequently reacted with AA3 to give the corresponding 2-aminoimidazoline. Boc protection of the 2-aminoimidazoline intermediate followed by saponification yielded AH3, which was converted to Compounds 28, 29, 31, 35, 39 and 40 by analogy to intermediate AA4 in Scheme AA.

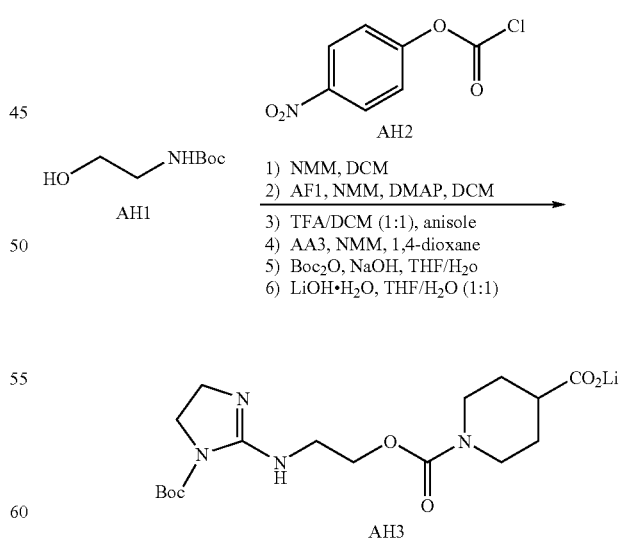

Similarly, conversion of AD2 to the corresponding chloroformate (AH4) followed by reaction with AH5 and saponification provided Compound 10.

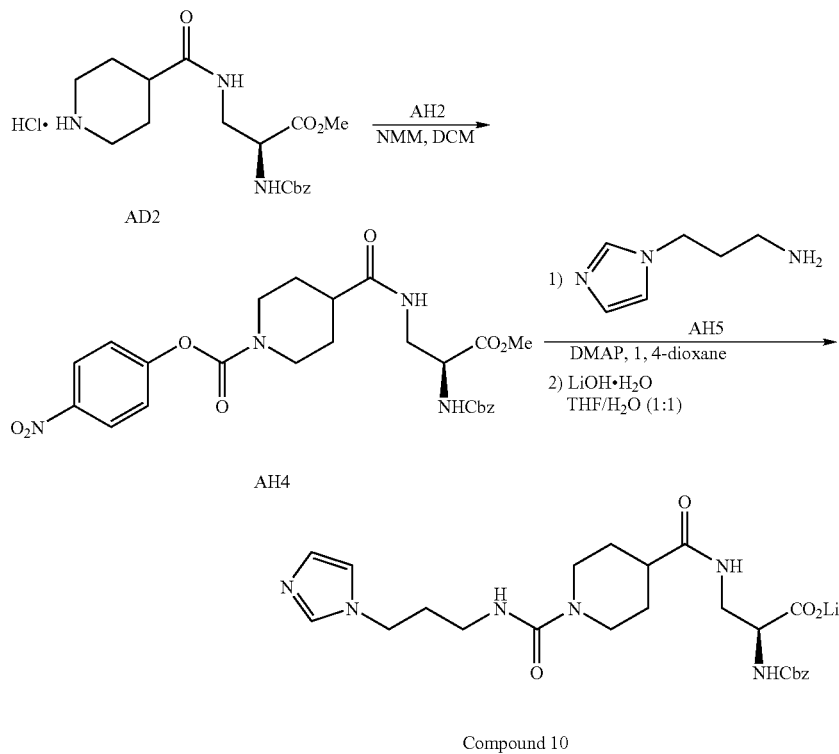

Compound 10

Specific Synthetic Methods

The following Examples are set forth to aid in the understanding of the invention, and are not intended and should not be construed to limit in any way the invention set forth in the claims which follow thereafter.

Protected amino acids were purchased from Bachem Bioscience Inc. N-α-Cbz-L-2,3-diaminopropionic acid was purchased from Fluka. Aromatic aldehydes were purchased from Aldrich Chemical Company, as were all other chemicals. High field $^1$H NMR spectra were recorded on a Bruker AC-360 spectrometer at 360 MHz, and coupling constants are given in Hertz. Melting points were determined on a Mel-Temp II melting point apparatus and are uncorrected. Microanalyses were performed at Robertson Microlit Laboratories, Inc., Madison, N.J. and are expressed in percentage by weight of each element per total molecular weight. In those cases where the product is obtained as a salt, the free base is obtained by methods known to those skilled in the art, e.g. by basic ion exchange purification. Nuclear magnetic resonance (NMR) spectra for hydrogen atoms were measured in the indicated solvent with tetramethylsilane (TMS) as the internal standard on a Bruker AM-360 (360 MHz) spectrometer. The values are expressed in parts per million down field from TMS. The mass spectra (MS) were determined on a Micromass Platform LC single quadrupole mass analyser fitted with an electrospray ionisation source coupled to a Hewlett Packard 1050 HPLC and a Jones Chromatography diverter valve in the loop injection mode. Positive mode electrospray was used eluting with acetonitrile/water/acetic acid (50:50:1) flowing at 0.3 mL/min with a sprayer temperature of 120° C. and an inlet desolvation cone set to 40 kV.

Unless otherwise noted, the materials used in the examples were obtained from readily available commercial suppliers or synthesized by standard methods known to anyone skilled in the art of chemical synthesis. The substituent groups, which vary between examples, are hydrogen unless otherwise noted.

EXAMPLE 1

β-[[[1-[4-[(4,5-dihydro-1H-imidazol-2-yl)amino]-1-oxobutyl]-4-piperidinyl]carbonyl]amino]-, (β$^3$S)-3-quinolinepropanoic acid (Cpd 1)

A mixture of AA1 (2.0 g, HCl salt, 0.011 mol), CH$_2$Cl$_2$ (100 mL), 4-N-Boc-aminobutyric acid (2.3 g, 1 eq), NMM (2.4 mL, 2 eq), HOBT (10 mg), and EDC.HCl (3.2 g, 1.5 eq) was stirred at 5° C. for 1 h, the ice bath was removed, and stirred for 2 h. The reaction was diluted with saturated aqueous NH$_4$Cl (50 mL) and the layers were separated. The organic layer was washed with NaOH (0.5 N, 15 mL), dried (Na$_2$SO$_4$), and evaporated to give a glass (3.6 g, 0.011 mol). This glass was dissolved in CH$_2$Cl$_2$ (15 mL) and anisole (1 mL), treated with TFA (15 mL), and stirred for 2 h. The solution was evaporated to give an oil (AA2, 3.8 g). AA2 was dissolved in dioxane (40 mL), treated with NMM (2.4 mL, 2 eq) and 2-(3,5-dimethylpyrazolyl)-4,5-dihydroimidazole-.HBr (2.7 g, 1 eq), and heated at reflux for 2 h. This mixture was cooled to RT and filtered. The filtrate was treated with MeOH (80 mL), NMM (2.4 mL, 2 eq), di-tert-butyl dicarbonate (4.8 g, 2 eq), and sodium carbonate (2.4 g, 2 eq), and stirred for 3 days. The solvents were evaporated, and the residue was partitioned between CH$_2$Cl$_2$ (100 mL) and water (10 mL). The organic layer was dried (Na$_2$SO$_4$), evaporated, and the oil purified by silica gel chromatography (1% NH$_4$OH/10% MeOH/CH$_2$Cl$_2$) to give a tan glass (1.8 g). The tan glass (0.09 g, 0.0023 mol) was dissolved in THF (5 mL), cooled to 5° C., treated with aqueous LiOH (0.11 g in 15 mL water), and stirred for 2 h. The solvents were evaporated to give AA4 as a pale yellow solid (1.0 g). This solid was slurried with MeCN (100 mL), AA5 (0.82 g, 1 eq, prepared starting from quinoline-3-carboxaldehyde as reported in M. Costanzo et al., WO 97/41102), HOBT (0.19 g, 0.5 eq), NMM (0.87 mL, 3 eq), and HBTU (1.2 g, 1.2 eq) at 5° C., stirred for 6 h, diluted with saturated aqueous NH$_4$Cl (12 mL), and the MeCN evaporated. The residue was partitioned between CHCl$_3$ (100 mL) and water (15 mL) and filtered. The filtrate layers were separated, and the organic layer was dried (Na$_2$SO$_4$), evaporated, and purified by silica gel chromatography (1% NH$_4$OH/4% MeOH/7% EtOH/CH$_2$Cl$_2$) to give a clear glass (0.60 g). The glass was treated with water (12 mL) and HCl (conc., 10 mL), and stirred for 18 h. The aqueous HCl was evaporated, the resultant oil treated with MeCN (20 mL), and the precipitate collected and dried to afford 1 as a white foam: $^1$H NMR (DMSO-d$_6$) δ1.3 (m, 2 H), 1.6 (m, 4 H), 2.3 (m, 2 H), 2.6 (m, 1 H), 2.8 (m, 1 H), 3.1 (m, 6 H), 3.4 (m, 1 H), 3.7 (m, 3 H), 3.8 (m, 1 H), 4.0 (m, 2 H), 4.2 (m, 1 H), 5.3 (m, 1 H), 7.7 (t, J=4 Hz, 1 H), 7.9 (t, J=4 Hz, 1 H), 8.2 (m, 2 H), 8.3 (m, 1 H), 8.6 (m, 2 H), 9.2 (s, 1 H), 10.9 (m, 1 H); MS m/e 481.4 (MH$^+$); [α]$^{25}$D −42.1° (c 0.114, MeOH).

EXAMPLE 2

3-[[[1-[4-[(4,5-dihydro-1H-imidazol-2-yl)amino]-1-oxobutyl]-4-piperidinyl]carbonyl]amino]-N-[(phenylmethoxy)carbonyl]-L-alanine (Cpd 2)

Compound 2 was prepared as described for 1 from AA4 (0.10 g) and methyl N-α-Cbz-L-2,3-diaminopropionate.HCl (0.09 g), and isolated as a tan glass: $^1$H NMR (DMSO-d$_6$) δ1.3 (m, 1 H), 1.4 (m, 1 H), 1.7 (m, 4 H), 2.4 (m, 3 H), 2.6 (m, 2 H), 2.8 (t, J=4 Hz, 1 H), 3.0 (m, 1 H), 3.1 (m, 1 H), 3.3 (m, 2 H), 3.4 (m, 1 H), 3.8 (m, 2 H), 4.1 (t, J=4 Hz, 1 H), 4.3 (m, 1 H), 5.0 (t, J=7 Hz, 2 H), 7.3 (m, 5 H), 7.6 (m, 3 H), 8.0 (m, 3 H), 8.2 (m, 1 H); MS m/e 503.4 (MH$^+$).

EXAMPLE 3

6-chloro-β-[[[1-[4-[(4,5-dihydro-1H-imidazol-2-yl)amino]-1-oxobutyl]-4-piperidinyl]carbonyl]amino]-, (β$^3$S)-3-pyridinepropanoic acid (Cpd 3)

Compound 3 was prepared as described for 1 from AA4 (0.15 g) and methyl (3S)-amino-3-(6-chloro-3-pyridyl)propionate.2HCl (0.11 g; prepared starting from 6-chloropyridine-3-carboxaldehyde as reported by M. Costanzo et al. in WO 97/41102), and isolated as a clear glass: $^1$H NMR (DMSO-d$_6$) δ1.2 (m, 4 H), 1.5 (m, 2 H), 2.2 (m, 3 H), 2.5 (m, 2 H), 2.7 (m, 2 H), 2.8 (m, 1 H), 3.1 (m, 1 H), 3.5 (m, 3 H), 3.8 (m, 1 H), 4.1 (m, 3 H), 4.3 (m, 1 H), 5.1 (m, 1 H), 7.4 (d, J=5 Hz, 1 H), 7.7 (d, J=5 Hz, 1 H), 8.1 (m, 3 H), 8.3 (s, 1 H), 8.5 (m, 1 H); MS m/e 464.9 (MH$^+$).

EXAMPLE 4

3-[[[1-[4-[(4,5-dihydro-1H-imidazol-2-yl)amino]-1-oxobutyl]-4-piperidinyl]carbonyl]amino]-, (3R)-butanoic acid (Cpd 4)

Compound 4 was prepared as described for 1 from AA4 (0.90 g) and tert-butyl (3R)-aminobutyrate (0.37 g, purchased from Oxford Asymmetry), and isolated as a clear glass: $^1$H NMR (DMSO-d$_6$) δ1.0 (d, J=5 Hz, 3 H), 1.3 (m, 2 H), 1.7 (m, 4 H), 2.3 (m, 6 H), 2.6 (m, 1 H), 3.0 (m, 1 H), 3.2 (m, 2 H), 3.6 (s, 4 H), 3.8 (m, 1 H), 4.0 (m, 1 H), 4.4 (m, 1 H), 7.8 (d, J=7 Hz, 2 H), 8.2 (m, 2 H); MS m/e 368.4 (MH$^+$).

EXAMPLE 5

β-[[[1-[3-[(4,5-dihydro-1H-imidazol-2-yl )amino]-2-methyl-1-oxopropyl]-4-piperidinyl]carbonyl]amino]-, (β$^3$S)-3-quinolinepropanoic acid (Cpd 5)

Compound 5 was prepared as described for 1 from N-Boc-imidazolin-2-yl-(3-aminoisobutyryl)-isonipecotic acid (0.10 g) and methyl N-α-Cbz-L-2,3-diaminopropionate.HCl (0.12 g), and isolated as glass: $^1$H NMR (DMSO-d$_6$) δ1.1 (d, J=6 Hz, 3 H), 1.3 (m, 1 H), 1.4 (m, 1 H), 1.7 (m, 4 H), 2.3 (m, 2 H), 2.6 (m, 2 H), 2.8 (m, 1 H), 3.0 (m, 2 H), 3.1 (m, 1 H), 3.3 (m, 2 H), 3.4 (m, 1 H), 3.8 (m, 1 H), 4.1 (m, 1 H), 4.3 (m, 1 H), 5.0 (t, J=7 Hz, 2 H), 7.3 (m, 5 H), 7.6 (m, 2 H), 8.0 (m, 3 H); MS m/e 503.4 (MH$^+$).

EXAMPLE 6

β-[[[1-[1-oxo-4-(2-pyridinylamino)butyl]-4-piperidinyl]carbonyl]amino]-, (β$^3$S)-3-quinolinepropanoic acid (Cpd 6)

A mixture of AC1 (2.0 g, 0.011 mol), CH$_2$Cl$_2$ (70 mL), and NMM (2.4 mL, 2 eq) at 5° C. was treated with 4-bromobutyryl chloride (1.3 mL, 1 eq), stirred for 6 h, and diluted with saturated aqueous NH$_4$Cl (15 mL). The organic layer was dried (Na$_2$SO$_4$), evaporated, and the resultant oil purified by silica gel chromatography (4% MeOH/CH$_2$Cl$_2$) to give an oil (1.8 g). The oil was dissolved in MeOH (10 mL) and isopropanol (15 mL) and then treated with 2-aminopyridine (0.70 g, 1.2 eq) and sodium carbonate (2 mg). This mixture was heated at reflux in a sealed flask for 2 h, cooled to RT, and evaporated to an oil. The oil was purified by silica gel chromatography (2% MeOH/3% EtOH/CH$_2$Cl$_2$) to give AC2 as a glass (0.3 g). Intermediate AC2 was saponified with lithium hydroxide and carried forward as exemplified in Scheme AA to give Compound 6 as clear flakes: $^1$H NMR (DMSO-d6) δ1.0-1.2 (m, 2 H), 1.7 (m, 4 H), 2.2 (m, 2 H), 3.0 (m, 3 H), 3.3 (m, 3 H), 3.5 (t, J=4 Hz, 1 H), 3.9 (m, 2 H), 5.5 (t, J=4 Hz, 1 H), 6.9 (m, 1 H), 7.1 (m, 1 H), 7.9 (m, 4 H), 8.0 (t, J=4 Hz, 1), 8.2 (m, 2 H), 8.8 (m, 3 H), 9.2 (s, 1 H), 10.9 (m, 1 H), 13.5 (m, 1 H); mp 87-90° C.; MS m/e 490 (MH$^+$).

EXAMPLES 7-62

Using the procedures described in Examples 1-6 or outlined in Schemes AA-AH and the appropriate reagents and starting materials known to those skilled in the art, other compounds of the present invention may be prepared including, but not limited to:

| Cpd | Sch | Salt | MH$^+$ |
|---|---|---|---|
| 7 | AC | TFA | 500 |
| 8 | AC | TFA | 522 |
| 9 | AA | Li | 439 |
| 10 | AH | Li | 501 |
| 11 | AA | TFA | 529 |
| 12 | AA | TFA | 489 |
| 13 | AC | Li | 507 |
| 14 | AA | TFA | 527 |
| 15 | AC | TFA | 499 |
| 16 | AA | TFA | 503 |
| 17 | AA | TFA | 527 |
| 18 | AA | TFA | 614 |
| 19 | AA | TFA | 534 |
| 20 | AA | HCl | 436 |

-continued

| Cpd | Sch | Salt | MH+ |
|-----|-----|------|-----|
| 21 | AA | HCl | 474 |
| 22 | AA | HCl | 444 |
| 23 | AA | HCl | 472 |
| 24 | AA | HCl | 490 |
| 25 | AA | HCl | 431 |
| 26 | AA | HCl | 499 |
| 27 | AA | HCl | 498 |
| 28 | AH | HCl | 505 |
| 29 | AH | HCl | 476 |
| 30 | AC | HCl | 440 |
| 31 | AH | HCl | 433 |
| 32 | AA | HCl | 448 |
| 33 | AA | HCl | 431 |
| 34 | AA | HCl | 490 |
| 35 | AH | HCl | 468 |
| 36 | AA | HCl | 480 |
| 37 | AA | HCl | 480 |
| 38 | AA | HCl | 466 |
| 39 | AH | HCl | 483 |
| 40 | AH | HCl | 433 |
| 41 | AC | HCl | 526 |
| 42 | AA | HCl | 517 |
| 43 | AA | HCl | 466 |
| 44 | AA | HCl | 495 |
| 45 | AA | — | 694 |
| 46 | AA | HCl | 594 |
| 47 | AA | TFA | 517 |
| 48 | AA | TFA | 458 |
| 49 | AA | TFA | 529 |
| 50 | AA | TFA | 461 |
| 51 | AA | HCl | 517 |
| 52 | AA | HCl | 431 |
| 53 | AA | TFA | 551 |
| 54 | AA | TFA | 517 |
| 55 | AA | HCl | 501 |
| 56 | AA | HCl | 435 |
| 57 | AG | HCl | 520 |
| 58 | AE | HCl | 479 |
| 59 | AF | HCl | 568 |
| 60 | AE | HCl | 505 |
| 61 | AE | HCl | 476 |
| 62 | AC | HCl | 483 |

EXAMPLE 63

As a specific embodiment of an oral composition, 100 mg of the compound 1 of Example 1 is formulated with sufficient finely divided lactose to provide a total amount of 580 to 590 mg to fill a size O hard gel capsule.

EXAMPLE 64

In Vitro Solid Phase Purified αvβ3 Binding Assay

The vitronectin/αvβ3 binding assay methods were derived from Mehta et al. (*Biochem J*. 1998, 330, 861). Human αvβ3 (Chemicon International Inc., Temecula, Calif.), at a concentration of 1 µg/ml dissolved in Tris buffer (20 mM Tris, 1 mM $CaCl_2$, mM $MgCl_2$, 10 µM $MnCl_2$, 150 mM NaCl), was immobilized on Immulon 96 well plates (Dynex Technologies, Chantilly, Va.) overnight at 4° C. Plates were washed and treated with blocking buffer (3% BSA in Tris buffer) for 2 h at 37° C. Plates were then rinsed 2 times with Tris buffer containing 0.3% BSA and 0.2% Tween20 (polyoxyethylenesorbitan monolaurate). Five minutes prior to the addition of 5 nM vitronectin (Sigma, St. Louis, Mo.), synthesized compounds were added to wells in duplicate. Each plate included c-RGDfV as an internal control. Following a 3 hour incubation at 37° C., plates were washed 5 times in assay buffer. An anti-human vitronectin IgG rabbit polyclonal antibody (Calbiochem, San Diego, Calif.) was added (1:2000) and plates were incubated for 1 hour at room temperature. VectaStain ABC peroxidase kit reagents (Vector Laboratories, Burlingame, Calif.) employing a biotin labeled anti-rabbit IgG, were utilized for detection of bound antibody. Plates were read at 490 nm on a Molecular Devices (Sunnyvale, Calif.) microplate reader. Table 1 shows the results of the in vitro solid phase purified αvβ3 binding assay for representative compounds of the present invention.

EXAMPLE 65

In Vitro Solid Phase Purified GP IIB/IIIA Binding Assay

A 96 well Immulon-2 microtiter plate (Dynatech-Immulon) was coated with 50 µl/well of RGD-affinity purified GPIIb/IIIa (effective range 0.5-10 µg/mL) in 10 mM HEPES, 150 mM NaCl, 1 mM $MgCl_2$ at pH 7.4. The plate was covered and incubated overnight at 4° C. The GPIIb/IIIa solution was discarded and 150 µl of 5% BSA was added and incubated at RT for 1-3 h. The plate was washed extensively with modified Tyrodes buffer. Biotinylated fibrinogen (25 µl/well) at 2× final concentration was added to the wells that contain the test compounds (25 µl/well). The plate was covered and incubated at RT for 2-4 h. Twenty minutes prior to incubation completion, one drop of Reagent A (VectaStain ABC Horse Radish Peroxidase kit, Vector Laboratories, Inc.) and one drop Reagent B were added with mixing to 5 mL modified Tyrodes buffer mix and let stand. The ligand solution was discarded and the plate washed (5×200 µl/well) with modified Tyrodes buffer. Vecta Stain HRP-Biotin-Avidin reagent (50 µl/well, as prepared above) was added and incubated at RT for 15 min. The Vecta Stain solution was discarded and the wells washed (5×200 µl/well) with modified Tyrodes buffer. Developing buffer (10 mL of 50 mM citrate/phosphate buffer @ pH 5.3, 6 mg o-phenylenediamine, 6 µl 30% $H_2O_2$; 50 µl/well) was added and incubated at RT for 3-5 min, and then 2 $NH_2SO_4$ (50 µl/well) was added. The absorbance was read at 490 nM. Table 1 shows the results of the in vitro solid phase purified GPIIb/IIIa binding assay for representative compounds of the present invention.

EXAMPLE 66

In Vitro Solid Phase Purified αvβ5 Binding Assay

The vitronectin/αvβ5 binding assay method was performed in the same manner as the vitronectin/αvβ3 binding assay (EXAMPLE 64) immobilizing with 1 µg/ml of human purified αvβ5 (Chemicon International, Inc.) on to Immulon 96 well plates (Dynex Technologies) instead of αvβ3. All other aspects of the assay including buffers, reagents, and incubation times remain unchanged.

TABLE I

| No. | $α_vβ_3$ $IC_{50}$ (uM) | IIb/IIIa $IC_{50}$ (uM) | $α_vβ_5$ $IC_{50}$ (uM) |
|-----|------|------|------|
| 1 | 0.0037 | 0.030 | 0.025 |
| 2 | 0.0058 | 0.0089 | 0.021 |
| 3 | 0.028 | 0.13 | NT |
| 4 | 0.15 | 1.70 | NT |
| 5 | 0.015 | 0.023 | NT |
| 6 | 0.0040 | 0.46 | NT |
| 7 | 0.49 | 7.9 | NT |
| 8 | 0.55 | 1.1 | NT |
| 9 | 30 | 0.30 | NT |
| 10 | >50 | 0.95 | NT |
| 11 | 1.3 | 0.0026 | NT |

TABLE I-continued

| No. | $\alpha_v\beta_3$ IC$_{50}$ (uM) | IIb/IIIa IC$_{50}$ (uM) | $\alpha_v\beta_5$ IC$_{50}$ (uM) |
|---|---|---|---|
| 12 | 0.020 | 0.014 | NT |
| 13 | 10 | 29 | NT |
| 14 | 0.050 | 0.0092 | NT |
| 15 | >5 | 17 | NT |
| 16 | 0.019 | 0.018 | 0.038 |
| 17 | 0.38 | 0.0054 | NT |
| 18 | 0.050 | 0.015 | NT |
| 19 | 0.32 | 0.071 | NT |
| 20 | 0.53 | 4.9 | NT |
| 21 | 0.023 | 0.41 | NT |
| 22 | >0.5 | 38 | NT |
| 23 | >0.5 | 7.3 | NT |
| 24 | 0.064 | 2.2 | NT |
| 25 | 0.032 | 2.9 | NT |
| 26 | 0.12 | 1.8 | NT |
| 27 | >0.5 | 13 | NT |
| 28 | 0.0082 | 1.5 | NT |
| 29 | 0.034 | 0.21 | NT |
| 30 | 0.14 | 56 | NT |
| 31 | 0.029 | 4.2 | NT |
| 32 | 0.12 | 3.6 | NT |
| 33 | 0.019 | 1.8 | NT |
| 34 | 0.029 | 1.5 | >5.0 |
| 35 | 0.14 | 1.6 | NT |
| 36 | >0.3 | 12 | NT |
| 37 | 0.29 | 1.7 | NT |
| 38 | >0.3 | 3.3 | NT |
| 39 | 0.0023 | 0.036 | NT |
| 40 | 0.012 | 1.1 | NT |
| 41 | >0.3 | 0.11 | NT |
| 42 | 0.17 | 0.14 | NT |
| 43 | 0.23 | 1.3 | NT |
| 44 | 0.028 | 0.36 | 2.9 |
| 45 | 3.7 | 14 | 40%* |
| 46 | 0.15 | 1.6 | >5 |
| 47 | 0.0040 | 0.028 | NT |
| 48 | 0.51 | 1.1 | NT |
| 49 | 0.039 | 0.012 | 0.21 |
| 50 | 3.9 | 0.0074 | 38%* |
| 51 | 0.27 | 0.29 | 2 |
| 52 | 0.25 | 2.7 | 0.76 |
| 53 | 0.57 | 0.0015 | NT |
| 54 | 0.072 | 0.013 | NT |
| 55 | 0.012 | 0.026 | 0 |
| 56 | >5 | 0.049 | NT |
| 57 | 0.35 | 0.13 | NT |
| 58 | 0.040 | 0.26 | 0.071 |
| 59 | 0.16 | 0.51 | NT |
| 60 | 0.027 | 0.19 | 0.086 |
| 61 | 0.18 | 2.7 | NT |
| 62 | >0.50 | 0.38 | NT |

*Percent inhibition at 5 μM.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

What is claimed is:

1. A compound of the Formula I

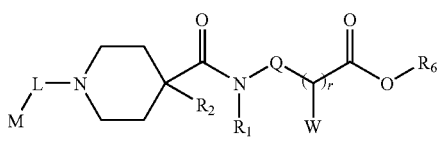

wherein
M is selected from the group consisting of:
  ethylene (optionally substituted within the carbon chain with methyl and substituted on the terminal carbon with one substituent selected from A),
  propylene (optionally substituted within the carbon chain with methyl, ethenyl, cyclohexylidene [wherein a ring carbon atom forms the point of attachment to the carbon chain] or 4-Cl-phenyl and substituted on the terminal carbon with one substituent selected from A),
  allylene (substituted with one substituent selected from A),
  piperidin-4-ylene (optionally substituted with one substituent selected from A), 1,4,5-dihydro-2-cyclopent-2-en-1-ylene (substituted with one substituent selected from A), and
  4-methylenephenyl (substituted on methylene with one substituent selected from A);
A is selected from the group consisting of:
  1H-imidazol-1-yl,
  1H-imidazol-2-yl,
  4,5-dihydro-1H-imidazol-2-yl (optionally substituted with a substituent selected from $C_1$-$C_4$ alkoxycarbonyl or aryl($C_1$-$C_4$)alkoxycarbonyl),
  pyridin-2-yl (optionally substituted with a substituent selected from $C_1$-$C_4$ alkyl,
    heteroaryl [optionally substituted with $C_1$-$C_4$ alkyl],
    halogen,
    hydroxy,
    nitro,
    cyano,
    amino,
    amino($C_1$-$C_4$)alkyl,
    $C_1$-$C_4$ alkylamino($C_1$-$C_4$)alkyl,
    di($C_1$-$C_4$ alkyl)amino($C_1$-$C_4$)alkyl),
  pyrimidin-2-yl,
  1,4,5,6-tetrahydro-pyrimidin-2-yl (optionally substituted with one to two substituents independently selected from the group consisting of $C_1$-$C_4$ alkyl, hydroxy and amino),
  piperidin-4-yl,
  benzimidazol-2-yl,
  1,2,3,4-tetrahydro-1,8-naphthyridin-7-yl,
  3H-imidazo[4,5-b]pyridin-2-yl,
  ($C_1$-$C_6$ alkyl)amino,
  (1H-imidazol-1-yl)amino,
  (1H-imidazol-2-yl)amino,
  (4,5-dihydro-1H-imidazol-2-yl)amino (optionally substituted on 4,5-dihydro-1H-imidazol-2-yl with a substituent selected from the group consisting of $C_1$-$C_6$ alkoxycarbonyl and aryl($C_1$-$C_6$)alkoxycarbonyl),
  (pyridin-2-yl)amino (optionally substituted on pyridin-2-yl with a substituent selected from the group consisting of
    $C_1$-$C_4$ alkyl,
    heteroaryl [optionally substituted with $C_1$-$C_4$ alkyl],
    halogen,
    hydroxy,
    nitro, cyano,
    amino,
    amino($C_1$-$C_4$)alkyl,
    $C_1$-$C_4$ alkylamino($C_1$-$C_4$)alkyl and
    di($C_1$-$C_4$ alkyl)amino($C_1$-$C_4$)alkyl),
  (pyrimidin-2-yl)amino,
  (1,4,5,6-tetrahydro-pyrimidin-2-yl)amino (optionally substituted on 1,4,5,6-tetrahydro-pyrimidin-2-yl with one to two substituents independently selected from the group consisting of $C_1$-$C_4$ alkyl, hydroxy or and amino), (4,5,6,7-tetrahydro-1H-1,3-diazepin-2-yl)amino,
(thiazol-2-yl)amino,
(benzimidazol-2-yl)amino,
(3H-imidazo[4,5-b]pyridin-2-yl)amino,
$R_3HNC(=NH)NH—$,
$R_3HNC(=O)NH—$,
(4,5,6,7-tetrahydro-1H-1,3-diazepin-2-yl)aminooxy,
(4,5-dihydro-1H-imidazol-2-yl)aminooxy, and
$R_3HNC(=NH)NHO—$;
with the proviso that when Q is —CH$_2$— and A is $R_3HNC(=NH)NH—$, $R_3$ is not H;
L is selected from the group consisting of —C(=O)—, —OC(=O)— and —HNC(=O)—;
$R_1$ is selected from the group consisting of hydrogen and $C_1$-$C_4$ alkyl;
$R_2$ is hydrogen;
$R_3$ is selected from the group consisting of hydrogen, $C_1$-$C_8$ alkyl, aryl($C_1$-$C_8$)alkyl and hydroxy;
Q is selected from the group consisting of —CH$_2$—, —CH($C_1$-$C_8$alkyl)—, —CH(aryl)-(wherein aryl is optionally substituted with one to five substituents independently selected from the group consisting of $C_1$-$C_4$ alkyl, $C_1$-$C_4$ alkoxy, —O—($C_1$-$C_3$ alkyl)-O—, halogen, hydroxy and trihalo($C_1$-$C_3$)alkyl), —CH(heteroaryl)-(wherein heteroaryl is optionally substituted with a substituent selected from halogen) and —CH(aryl($C_1$-$C_8$)alkyl)-;
W is selected from the group consisting of hydrogen and N(R$_4$)T;
r is 1;
$R_4$ is selected from the group consisting of hydrogen and $C_1$-$C_4$ alkyl;
T is selected from the group consisting of $R_5$C(=O)— and $R_5$OC(=O)—;
$R_5$ is selected from the group consisting of aryl and aryl($C_1$-$C_4$)alkyl;
$R_6$ is selected from the group consisting of hydrogen, methyl and $(R_8)(R_7)NC(=O)CH_2$; and,
$R_7$ and $R_8$ are independently selected from the group consisting of hydrogen, methyl and ethyl;
and pharmaceutically acceptable salts thereof.

2. The compound of claim 1 selected from the group consisting of:
β-[[[1-[4-[(4,5-dihydro-1H-imidazol-2-yl)amino]-1-oxobutyl]-4-piperidinyl]carbonyl]amino]-(β$^3$S)-3-quinolinepropanoic acid;
β-[[[1-[1-oxo-4-(2-pyridinylamino)butyl]-4-piperidinyl]carbonyl]amino]-(β$^3$S)-3-quinolinepropanoic acid;
4-[[[(2S)-2-carboxy-2-[[(phenylmethoxy)carbonyl]amino]ethyl]amino]carbonyl]-2-[(4,5-dihydro-1H-imidazol-2-yl)amino]ethyl ester 1-piperidinecarboxylic acid;
β[[[1-[[2-[(4,5-dihydro-1H-imidazol-2-yl)amino]ethoxy]carbonyl]-4-piperidinyl]carbonyl]amino]-(β$^3$S)-3-quinolinepropanoic acid;
β-[[[1-[3-[[(4,5-dihydro-1H-imidazol-2-yl)amino]oxy]-1-oxopropyl]-4-piperidinyl]carbonyl]amino]-1,3-benzodioxole-5-propanoic acid; and,
β[[[1-[1-oxo-4-(2-pyridinylamino)butyl]-4-piperidinyl]carbonyl]amino]-1,3-benzodioxole-5-propanoic acid;
and pharmaceutically acceptable salts thereof.

3. The compound of claim 1 selected from the group consisting of:
6-chloro-β-[[[1-[4-[(4,5-dihydro-1H-imidazol-2-yl)amino]-1-oxobutyl]-4-piperidinyl]carbonyl]amino]-(β$^3$S)-3-pyridinepropanoic acid;
β-[[[1-[3-[(4,5-dihydro-1H-imidazol-2-yl)amino]-2-methyl-1-oxopropyl]-4-piperidinyl]carbonyl]amino]-(β$^3$S)-3-quinolinepropanoic acid, and β-[[[1-[1-oxo-4-(2-pyridinylamino)butyl]-4-piperidinyl]carbonyl]amino]-(β$^3$S)-3-quinolinepropanoic acid.

4. The compound of claim 1 selected from the group consisting of:
4-[[[(2S)-2-carboxy-2-[[(phenylmethoxy)carbonyl]amino]ethyl]amino]carbonyl]-2-[(4,5-dihydro-1H-imidazol-2-yl)amino]ethyl ester 1-piperidinecarboxylic acid, and
β-[[[1-[[2-[(4,5-dihydro-1H-imidazol-2-yl)amino]ethoxy]-carbonyl]-4-piperidinyl]carbonyl]amino]-(β$^3$S)-3-quinolinepropanoic acid.

5. The compound of claim 1 which is:
(β$^3$S)-6-chloro-β-[[[1-[[1-[[(4,5-dihydro-1H-imidazol-2-yl)amino]methyl]cyclohexyl]acetyl]-4-piperidinyl]carbonyl]amino]-3-pyridinepropanoic acid.

6. The compound of claim 1 which is:
β-[[[1-[4-[[4,5-dihydro-1-[(2-methylpropoxy)carbonyl]-1H-imidazol-2-yl]amino]-1-oxobutyl]-4-piperidinyl]carbonyl]amino]-3-quinolinepropanoic acid 2-(diethylamino)-2-oxoethyl ester.

7. A pharmaceutical composition comprising a compound of claim 1 and a pharmaceutically acceptable carrier.

8. A process for making a pharmaceutical composition comprising mixing a compound of claim 1 and a pharmaceutically acceptable carrier.

9. A method of treating an αvβ3, αvβ5 or GPIIb/IIIa integrin-mediated disorder selected from the group consisting of restenosis, unstable angina, re-occlusion following thrombolytic therapy, re-occlusion following angioplasty, and osteoporosis, in a subject in need thereof comprising administering to the subject a therapeutically effective amount of a compound of claim 1.

10. The method of claim 9 wherein the therapeutically effective amount of the compound is between about 0.01 mg/kg/day and about 300 mg/kg/day.

11. A method of treating an αvβ3, αvβ5 or GPIIb/IIIa integrin-mediated disorder selected from the group consisting of restenosis, unstable angina, re-occlusion following thrombolytic therapy, re-occlusion following angioplasty, and osteoporosis, in a subject in need thereof comprising administering to the subject a therapeutically effective amount of a pharmaceutical composition of claim 7.

12. The method of claim 11, wherein the therapeutically effective amount of the pharmaceutical composition is between about 0.01 mg/kg/day and about 300 mg/kg/day.

13. The compound of claim 1 which is:
β-[[[1-[4-[(4,5-dihydro-1H-imidazol-2-yl)amino]-1-oxobutyl]-4-piperidinyl]carbonyl]amino]-(β$^3$S)-3-quinolinepropanoic acid.

14. The method of claim 9 wherein said αvβ3, αvβ5 or GPIIb/IIIa integrin-mediated disorder is osteoporosis.

15. The method of claim 11 wherein said αvβ3, αvβ5 or GPIIb/IIIa integrin-mediated disorder is osteoporosis.

16. A method of claim 9 wherein the αvβ3, αvβ5 or GPIIb/IIIa integrin-mediated disorder is selected from the group consisting of restenosis, unstable angina, re-occlusion following thrombolytic therapy, and re-occlusion following angioplasty.

17. A method of claim 11 wherein the αvβ3, αvβ5 or GPIIb/IIIa integrin-mediated disorder is selected from the group consisting of restenosis, unstable angina, re-occlusion following thrombolytic therapy, and re-occlusion following angioplasty.

* * * * *